(12) United States Patent
Critchlow et al.

(10) Patent No.: US 6,520,930 B2
(45) Date of Patent: Feb. 18, 2003

(54) INJECTORS, INJECTOR SYSTEMS AND INJECTOR CONTROL

(75) Inventors: Richard G. Critchlow, Oakmont, PA (US); Martin J. Uram, Pittsburgh, PA (US); David A. Mishler, Slippery Rock, PA (US); Richard A. Bates, Pittsburgh, PA (US); Robert J. Doiron, Nova Scotia (CA)

(73) Assignee: Medrad, Inc., Indianola, PA (US)

( * ) Notice: Subject to any disclaimer, the term of this patent is extended or adjusted under 35 U.S.C. 154(b) by 15 days.

(21) Appl. No.: 09/826,430

(22) Filed: Apr. 3, 2001

(65) Prior Publication Data

US 2002/0016569 A1 Feb. 7, 2002

Related U.S. Application Data

(63) Continuation-in-part of application No. 09/721,427, filed on Nov. 22, 2000.
(60) Provisional application No. 60/167,309, filed on Nov. 24, 1999.

(51) Int. Cl.[7] .............................................. A61M 31/00
(52) U.S. Cl. .......................... 604/67; 604/154; 417/44.2
(58) Field of Search ................................ 604/131, 151, 604/154, 31, 65, 67; 417/16, 17, 44.2; 128/DIG. 7

(56) References Cited

U.S. PATENT DOCUMENTS

| | | | |
|---|---|---|---|
| 2,925,814 A | * | 2/1960 | Vibber et al. ......... 128/DIG. 7 |
| 3,701,345 A | | 10/1972 | Heilman et al. |
| 4,006,736 A | | 2/1977 | Kranys et al. |
| 4,024,864 A | * | 5/1977 | Davies et al. ......... 128/DIG. 13 |
| 4,494,051 A | * | 1/1985 | Bailey ..................... 318/138 |
| 4,812,724 A | | 3/1989 | Langer et al. |
| 4,854,324 A | | 8/1989 | Hirschman et al. |
| 5,300,031 A | | 4/1994 | Neer et al. |
| 5,354,273 A | | 10/1994 | Hagen |
| 5,803,712 A | | 9/1998 | Davis et al. |
| 5,808,203 A | | 9/1998 | Nolan, Jr. et al. |
| 5,868,710 A | | 2/1999 | Battiato et al. |
| 6,225,904 B1 | * | 5/2001 | Jaffe et al. .............. 340/545.3 |
| 6,262,544 B1 | * | 7/2001 | Disser et al. ............ 318/138 |

FOREIGN PATENT DOCUMENTS

EP          0 402 553          12/1990

* cited by examiner

Primary Examiner—Manuel Mendez
Assistant Examiner—Mark Han
(74) Attorney, Agent, or Firm—Henry E. Bartony, Jr.; Gregory L. Bradley

(57) ABSTRACT

An injector for use in injecting a fluid in a medical injection procedure includes a drive having a motor to pressurize the fluid; a sensor to provide a measure of fluid pressure; and a pressure monitor in communication with the sensor and the drive to stop the motor using 4-quadrant control when the sensor communicates a measured pressure of at least a pressure hazard limit. The pressure monitor also limits power input to the motor to a power limit once the sensor communicates a measured pressure of at least a power limiting pressure. The power limiting pressure is below the pressure hazard limit.

13 Claims, 19 Drawing Sheets

INJECTORS, INJECTOR SYSTEMS AND INJECTOR CONTROL

RELATED REFERENCES

This patent application is a continuation in part of U.S. patent application Ser. No. 09/721,427, filed Nov. 22, 2000 (United States Express Mail Label No. EL317714945US) entitled INJECTORS, INJECTOR SYSTEMS, AND INJECTOR CONTROL, which claims priority to U.S. Provisional Application Ser. No. 60/167,309, filed on Nov. 24, 1999, the disclosures of which are incorporated herein by reference.

BACKGROUND OF THE INVENTION

The present invention relates generally to injectors, injector systems and control of injectors and injector systems, and, especially, to injectors, injector systems and injector control for use in medical procedures in which a fluid is injected into a patient.

In many medical diagnostic and therapeutic procedures, a physician or other person injects a patient with a fluid. In recent years, a number of injector-actuated syringes and powered injectors for pressurized injection of fluids such as contrast media have been developed for use in procedures such as angiography, computed tomography, ultrasound and NMR/MRI. In general, these powered injectors are designed to deliver a preset amount of contrast media at a preset flow rate.

To ensure the safety of the patient, the operation of a powered injector should be carefully controlled. For example, it is desirable not to exceed a certain fluid pressure during an injection procedure. In addition to potential hazards to the patient (for example, vessel damage) and potential degradation of the diagnostic and/or therapeutic utility of the injection fluid, excessive pressure can lead to equipment failure. For example, because of the potential of cross-contamination between patients, the syringe and tubing used to carry fluid to a patient are typically changed on a per-patient basis. Such disposable syringes and other fluid path components (sometimes referred to collectively as a "disposable set") are typically fabricated from plastics of various burst strengths. If the injector causes pressure in the fluid path to rise above the burst strength of a disposable fluid path element, the fluid path element will fail.

In controlling system or injection pressure, current injectors use motor current as an indication of system pressure. This technique has inherent accuracy problems, as there are many variables between the parameter being measured (motor current) and the parameter of interest (fluid pressure). These include, for example, measurement inaccuracies, motor torque constant variation, motor variation with temperature, frictional effects in the drive train, and frictional effects in the syringe. In general, any control algorithm must allow for such errors and must make a conservative estimate of fluid pressure to prevent actual fluid pressure from reaching a hazardous value.

Current systems typically predefine a conservative pressure (that is, motor current) control value. As the preset pressure control level is reached, such injectors begin to slow down the flow rate of injection in an effort to stop the build up pressure. At that point, an injector system that was originally intended to servo control the volume and flow rate of the injection fluid begins to servo control pressure. The inaccuracies inherent in using motor current to derive pressure result in a compliant system, and the operation of the servo in that state is oscillatory. Pressures in excess of desirable limits can occur, resulting in potentially hazardous operation of the injector.

In addition to problems of control with current injector systems, many such systems lack convenience and flexibility in the manner in which the injector systems must be operated. In that regard, the complexity of medical injection procedures and the hectic pace in all facets of the health care industry place a premium on the time and skills of an operator.

It is thus very desirable to develop injectors exhibiting improved operative control as well as injectors exhibiting improved ease of use.

SUMMARY OF THE INVENTION

In one aspect, the present invention provides an injector for use in injecting a fluid in a medical injection procedure. The injector includes a drive mechanism to pressurize the fluid; a sensor to measure a variable that is proportional to fluid pressure (that is, a direct or indirect measurement of fluid pressure); and a pressure monitor (for example, including hardwired circuitry and/or software) in communication with the sensor and the drive mechanism to stop the injection procedure when the sensor measures a value of the variable that corresponds to a pressure hazard limit.

Preferably, the pressure monitor further limits power input to the drive mechanism to a power limit once the variable reaches a value that corresponds to a power limiting pressure that is below the pressure hazard limit. In this manner, the pressure hazard limit should never be reached. If, however, the power limiting feature fails, the injector terminates the injection procedure once the pressure hazard limit is reached.

The drive mechanism may, for example, receive power from a motor. In this embodiment, the sensor can, for example, measure motor current. The pressure monitor can limit the motor current to a value corresponding to the power limiting pressure. The power limit is typically predetermined or preset for the injector in this embodiment.

In another embodiment, a more direct and accurate manner of measuring fluid pressure than measuring motor current is used. In one embodiment, for example, the sensor measures force exerted upon a component of the drive mechanism or an injector component in connection with the drive mechanism. In general, the sensor can measure force upon any component of the injector that bears a load proportional to the fluid pressure. Particularly in the case that a force sensor (for example, a strain gauge) or pressure transducer is used to measure fluid pressure, setting of the power limit during injector use and periodic auto-recalibration are facilitated.

In another aspect, the present invention provides an injector for use in injecting a fluid in a medical injection procedure including: a drive mechanism to pressurize the fluid; a sensor to measure a variable that is proportional to fluid pressure; and a pressure monitor in communication with the sensor and the drive mechanism to limit power input to the drive mechanism to a power limit once the variable reaches a value that corresponds to a power limiting pressure.

In a further aspect, the present invention provides an injector system for use in injecting a fluid in a medical injection procedure including a drive mechanism to pressurize the fluid and a control mechanism to control flow rate of the fluid and volume of the fluid injected. The injector further includes a sensor including a force transducer providing a measure of fluid pressure and a pressure monitor in communication with the sensor and the drive mechanism to stop the injection procedure when the sensor measures a pressure corresponding to a pressure hazard limit. The pressure monitor also preferably limits power input to the drive mechanism to a power limit when the sensor measures a pressure corresponding to a power limiting pressure. As discussed above, the power limiting pressure is less that the pressure hazard limit.

In another aspect, the present invention provides an injector system for use in injecting a fluid in a medical injection procedure including a drive mechanism to pressurize the fluid and a control mechanism to control flow rate of the fluid and volume of the fluid injected (typically on the basis of flow rate and volume setting input by the user of the injector using a data entry mechanism as known in the art). The injector also includes a safety system including a sensor (for example, a force transducer) to provide a measure of fluid pressure. The safety system also includes a pressure monitor in communication with the sensor and the drive mechanism. The pressure monitor is adapted to override settings of the control mechanism and stop the injection procedure when the sensor measures a pressure corresponding to a pressure hazard limit. Moreover, the pressure monitor is adapted to override settings of the control mechanism to limit power input to the drive mechanism to a power limit when the sensor measures a pressure corresponding to a power limiting pressure, the power limiting pressure being below the pressure hazard limit. In general, the power limit is preferably the power being supplied to the drive mechanism when the power limiting pressure is measured.

In a further aspect, the present invention provides a method of controlling an injector used in a medical injection procedure. The method includes the steps of:

measuring a variable that is proportional to fluid pressure; and limiting power input to a drive mechanism of the injector to a power limit once the variable reaches a value that corresponds to a power limiting pressure.

The method may also include the step of:

terminating the injection procedure if the value of the variable corresponds to a pressure hazard limit, the pressure hazard limit being greater than the power limiting pressure.

In another aspect, the present invention provides an injector for use with a syringe having a plunger disposed therein to inject a fluid in a medical procedure. The injector includes:

a control unit including a control unit housing and control circuitry disposed within the control unit housing; and at least one syringe interface module including, a module housing, at least one syringe interface on the module housing that is adapted to connect the syringe to the module housing and at least one drive member within the module housing to control motion of the plunger, the module housing being moveable relative to the control unit housing.

In one embodiment the module housing is rotatable relative to the control unit housing. In another embodiment the module housing is physically detached from the control unit housing.

In still a further aspect, the present invention provides a system for performing a medical imaging procedure including:

an injector, the injector including a portable remote control panel;

an imaging apparatus; and an attachment member in the vicinity of (or attached to) the imaging apparatus, the attachment member being adapted to attach or support the remote control panel in the vicinity of the imaging apparatus to facilitate generally simultaneous access by the operator to both the remote control panel and the imaging apparatus while performing the medical imaging procedure.

In another aspect, the present invention provides an injector for use in injecting a fluid in a medical injection procedure including a drive having a motor to pressurize the fluid; a sensor to provide a measure of fluid pressure; and a pressure monitor in communication with the sensor and the drive to stop the motor using 4-quadrant control when the sensor communicates a measured pressure of at least a pressure hazard limit. The pressure monitor also limits power input to the motor to a power limit once the sensor communicates a measured pressure of at least a power limiting pressure as described above. As also described above, the power limiting pressure is below the pressure hazard limit.

In another aspect, the present invention provides an injector system including a motor to pressurize the fluid; a servo controller in communication with the motor; a sensor including a force transducer to provide a measure of fluid pressure; and a pressure monitor in communication with the sensor and the servo controller to stop the motor using 4-quadrant control when the sensor measures a pressure of at least a pressure hazard limit. Once again, the pressure monitor preferably also limiting power input to the motor to a power limit when the sensor measures a pressure corresponding to a power limiting pressure, which is less than the pressure hazard limit.

In another aspect, the present invention provides an injector system including a motor to pressurize the fluid; a servo controller in communication with the motor; a sensor in communication with the servo controller including a force transducer to provide a measure of fluid pressure; and a safety monitoring system in communication with the sensor. The safety monitoring system is also in communication with the servo controller and sets a pressure hazard limit. The safety monitoring system communicates the pressure hazard limit to the servo controller. The servo controller stops the motor using 4-quadrant control when the sensor communicates a fluid pressure measurement of at least the pressure hazard limit.

Preferably, the safety monitoring system also sets a power limiting pressure that is less than the pressure hazard limit and communicates the power limiting pressure to the servo controller. The servo controller limits the power to the motor when the sensor communicates a measured pressure of at least the power limiting pressure.

In still another aspect, the present invention provides a method of controlling an injector system for use in a medical injection procedure including the steps of: measuring a variable that is proportional to fluid pressure; limiting power input to a motor of the injector to a power limit once the variable reaches a value corresponding to at least a power limiting pressure; and stopping the motor using 4-quadrant control if the variable reaches a value corresponding to at least a pressure hazard limit, the pressure hazard limit being greater than the power limiting pressure.

Numerous other objects and advantages of the present invention will be apparent from the following drawings and detailed description of the invention and its preferred embodiments.

DETAILED DESCRIPTION OF THE INVENTION

Figure 1A:
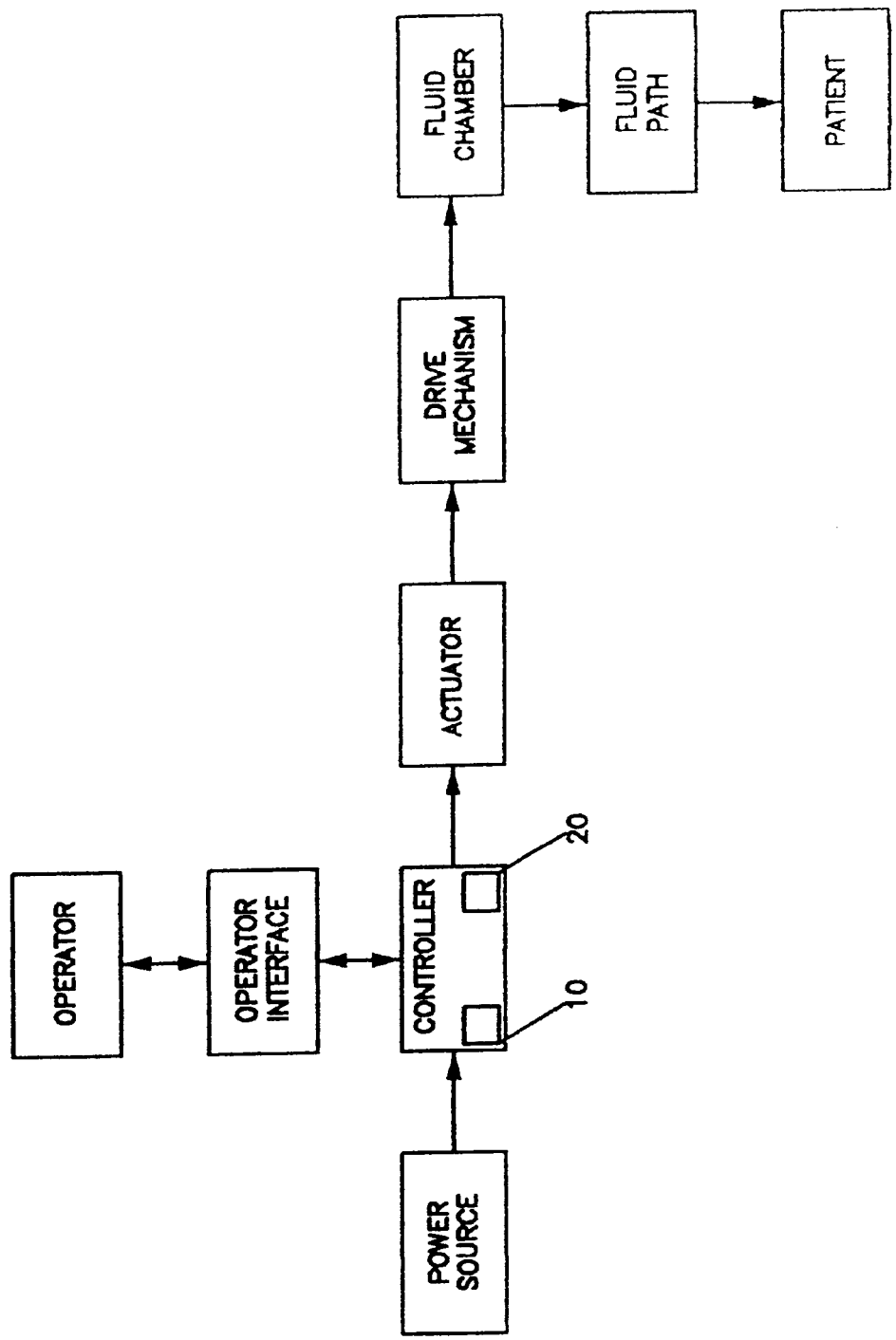
FIG. 1A illustrates a schematic representation of one embodiment of a fluid delivery system for use in the present invention.
Figure 5A:
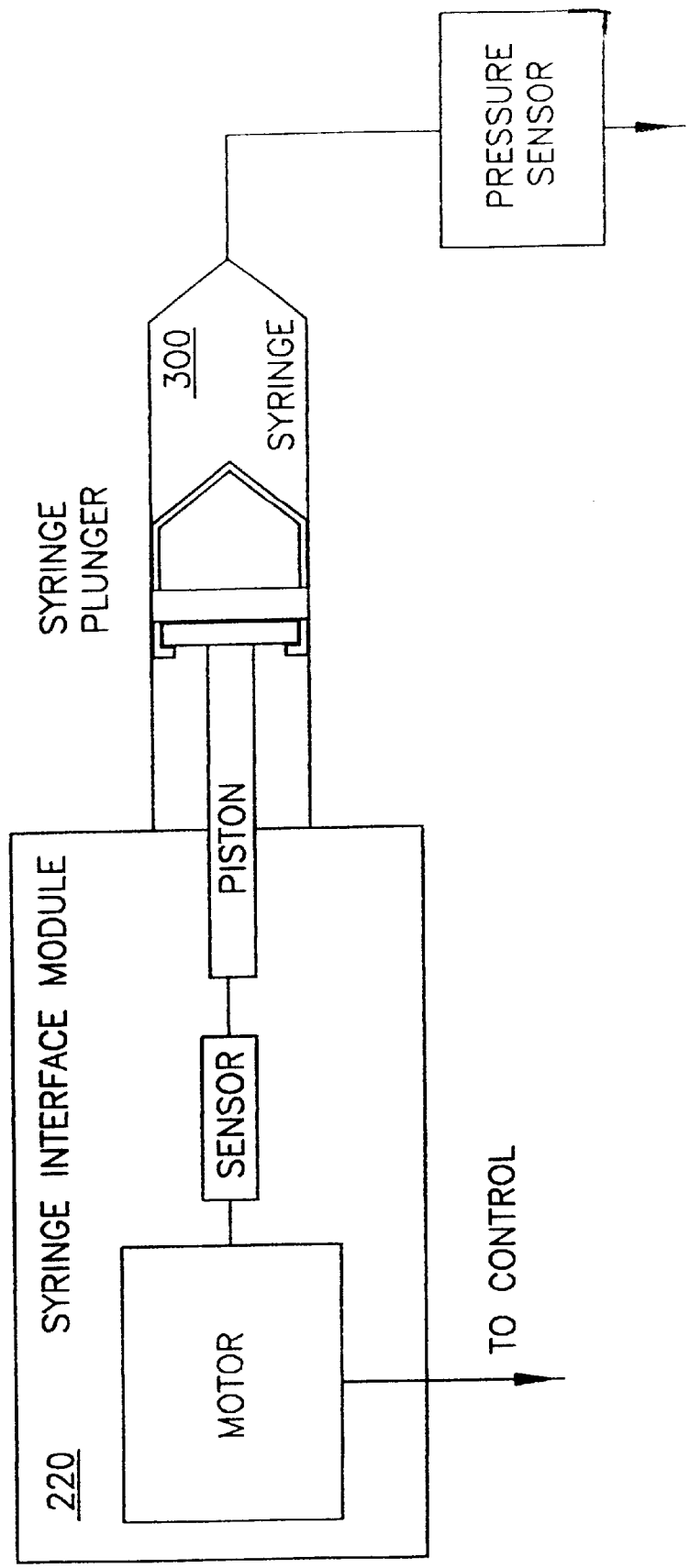
FIG. 5A illustrates a cross-sectional view of an embodiment of a syringe interface module in which fluid pressure is measured via a transducer/sensor.

FIG. 1A illustrates several components of a fluid delivery system for use in the present invention. The fluid delivery system includes an operator interface connected to a controller, which may include a computer (including, for example, a processing unit 10 and a memory 20), that is supplied by a power source. The power source may, for example, include a battery or other electrical power supply. In operation, the controller sends activation energy to the actuator, which powers a drive mechanism. The drive mechanism is connected to a fluid chamber such as a syringe (see, for example, FIG. 5A) that contains a volume of injection fluid to be pressurized. The fluid chamber connects to the patient through a fluid path. The fluid path may, for example, include sterile tubing that connects to the patient.

Unlike prior injectors, the control systems of the injectors of the present invention preferably treat pressure as a hazard, rather than as a variable to be controlled. For example, a pressure hazard limit can be set as a trip point in the present invention. When pressure in the system (as measured directly or indirectly) reaches the pressure hazard level, the injection may be terminated. Preferably, the performance of the injector is further limited in a manner to ensure that the user is not inconvenienced by continual shutdowns during normal operations. In one embodiment, the power delivered to the drive mechanism is limited in a manner so that the pressure hazard limit or upper hazard level is not reached.

Figure 1B:
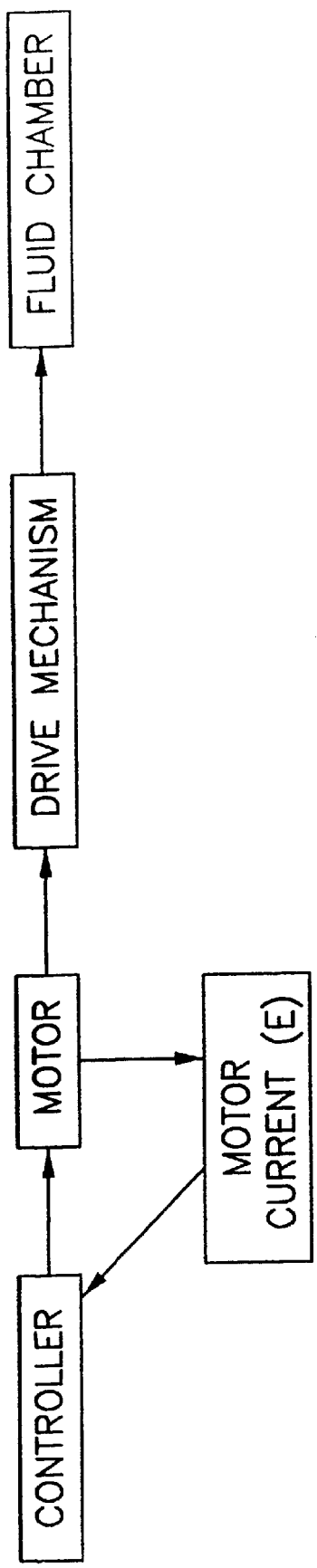
FIG. 1B illustrates an embodiment of pressure limiting through limiting motor current.

In the embodiment of FIG. 1B, for example, the actuator includes a DC brush type motor. The power delivered to the drive mechanism can be limited by presetting a clamp on the maximum current that can be delivered to the motor. The maximum current corresponds to a fluid pressure (the "power limiting pressure") that is below the pressure hazard limit. With the drive power limited to the set value (that is, the power limit), the injector will not be able to generate enough pressure to cause a hazard (that is, to reach the pressure hazard limit). If pressure in the system rises to the point where the injector enters a state of power limited operation (that is, the current has reached the set maximum current), operation of the injector will be smooth rather than oscillatory (as experienced with currently available injectors). Currently available injectors adjust the motor current based on both a sampled current and an actual, estimated or programmed flow rate of the delivery system. Unlike currently available injectors, the injector of the present invention is not tracking the operation of a compliant system, but is simply limiting current delivered to the motor to the maximum current. The injector control of the present invention thus results in improved smoothness of flow rate when the injector is in a limiting state of operation.

Motor current can be limited through electronic circuitry (as known in the art) that samples the motor current, compares the magnitude to the threshold set level and limits the applied current to the device. Motor current can, for example, be controlled by a pulse width modulation (PWM) type drive with a current limit comparator. As known in the art and used herein, the terms "pulse width modulation" or "PWM" refer to an encoding scheme in which a quantity is encoded by the proportion of a fixed time period in which a signal is held active. The proportion is referred to as the "duty cycle," and is often referred to in percent. In this embodiment, when motor current exceeds the set threshold power limit level, the PWM cycle in progress is preferably prematurely terminated and held off for a fixed time period, reducing current to the motor until the next cycle.

Figure 2:
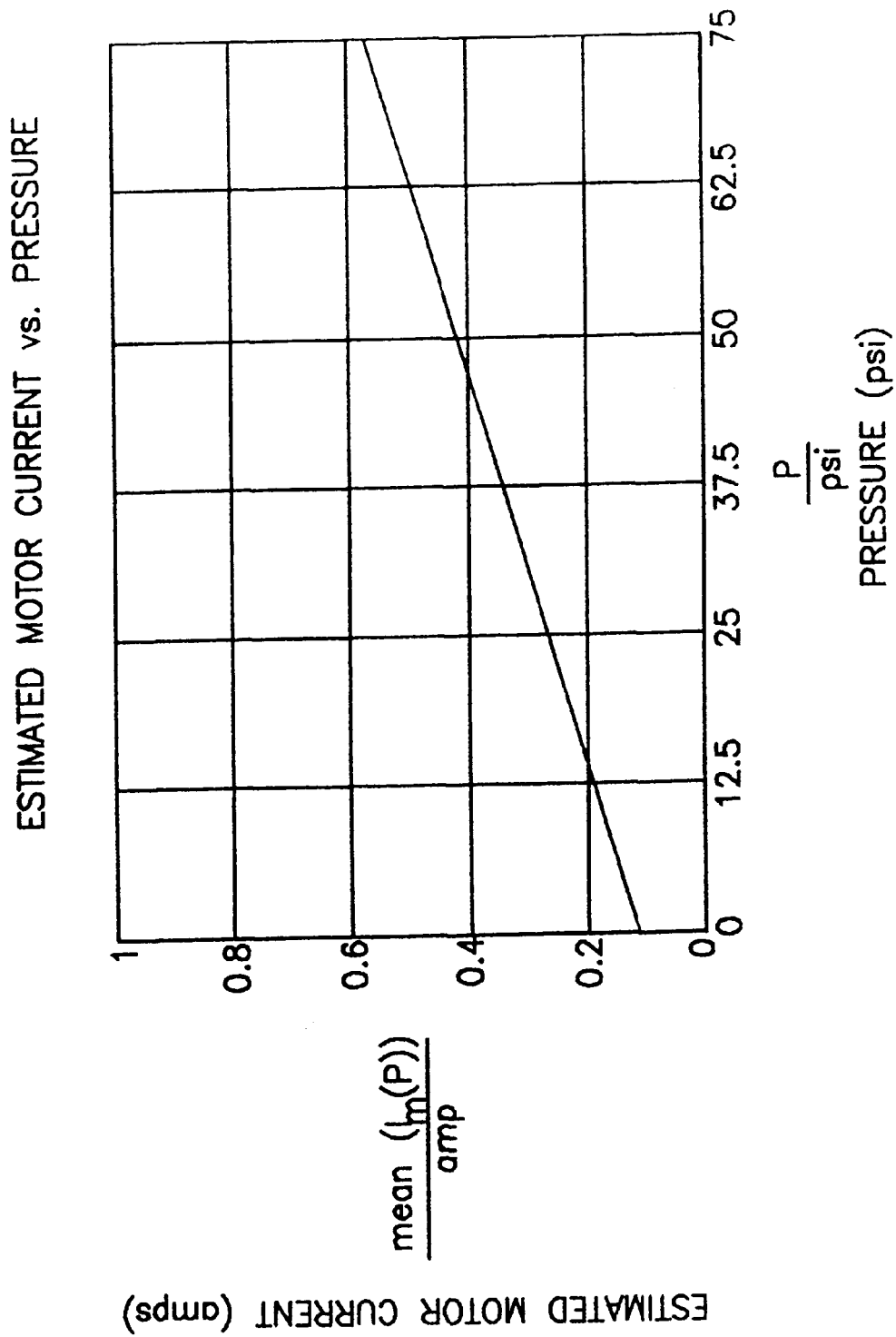
FIG. 2 illustrates the relationship between motor current and system pressure for an injector.

In effect, the control process of the present invention as described above limits output fluid power (flow rate× pressure) by limiting electrical input power (current× voltage) to the motor by limiting the maximum value of motor current. The relationship between motor current and pressure is illustrated in FIG. 2.

Figure 3A:
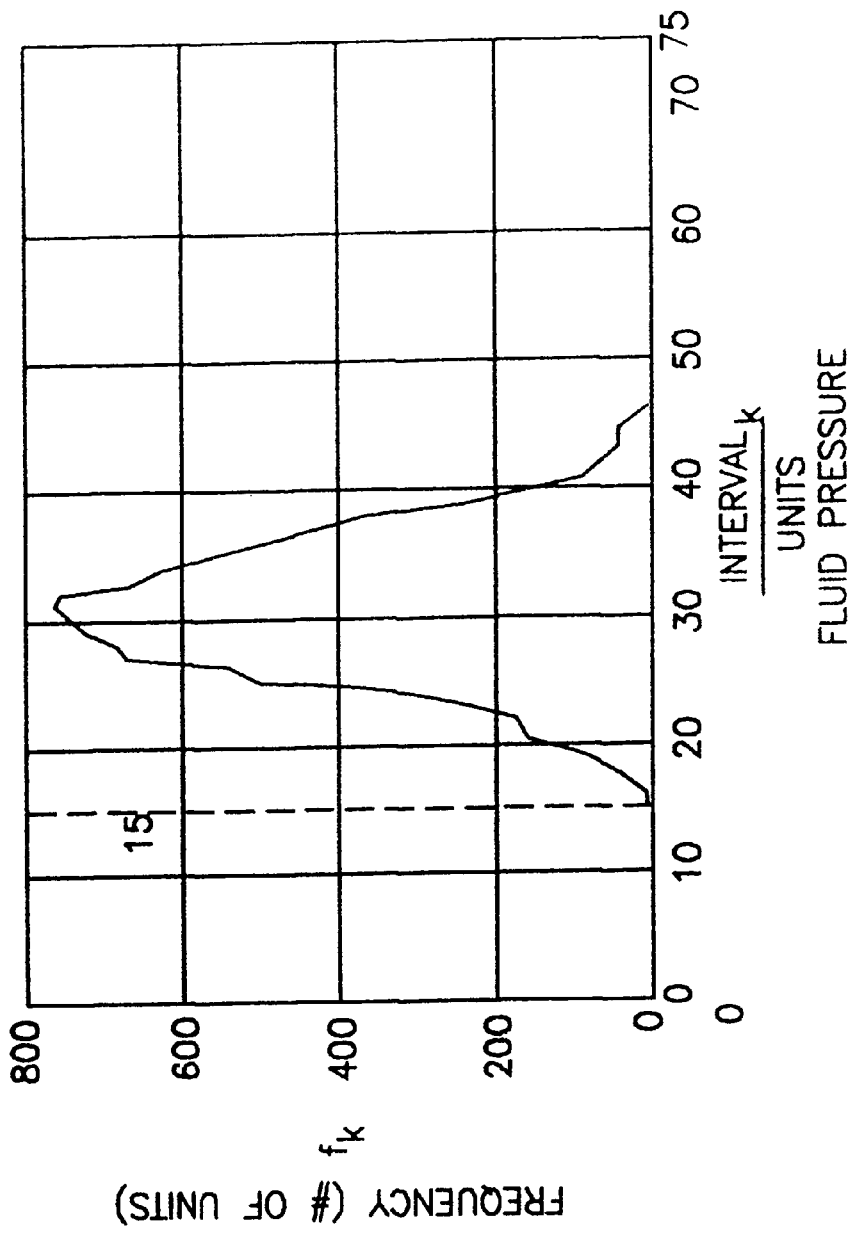
FIG. 3A illustrates a predicted maximum pressure distribution.

In one embodiment, the limit threshold for motor current was fixed at a single value for the injector and was not flow rate dependent. The variation in the predicted pressure was found to be small enough to allow all injector systems of a particular type to be constructed with such a fixed limit, thereby avoiding the need for pressure calibration. FIG. 3A illustrates a predicted maximum pressure distribution, given the statistical variations expected elsewhere in the injector system.

In one set of exemplary studies, the nominal pressure limit value (that is, power limiting pressure) was set between 20 and 50 psi (typically, at a midpoint of 37.5 psi). An over pressure monitoring circuit was set to trip at a pressure hazard limit or level between 50 and 75 psi (typically, 65.5 psi). In general, the power limiting pressure was chosen to fall in the center of the power or pressure limited operating range. The injector systems of FIGS. 1A through 3C operate over a range of pressures when power limited because of compliance in the system when measuring fluid pressure indirectly. This compliance will be discussed in greater detail below in connection with system specifications and calibration.

Figure 3B:
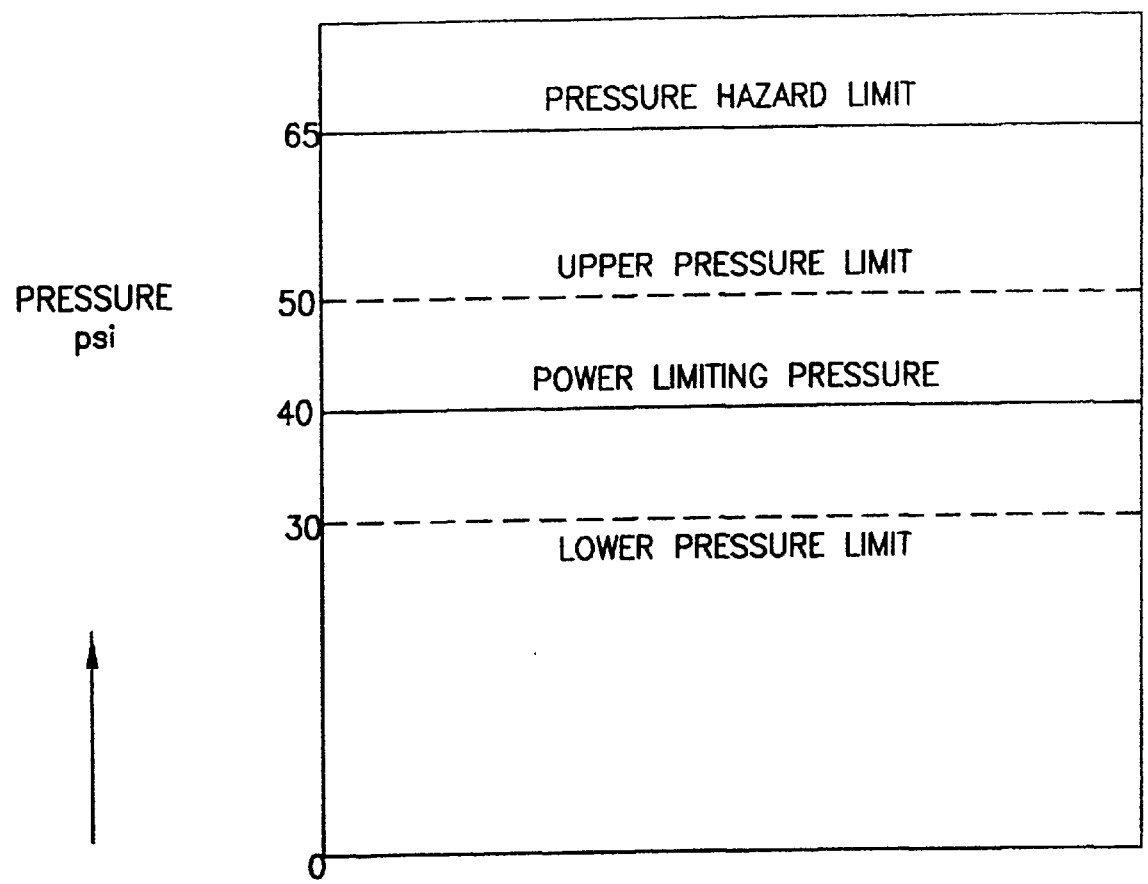
FIG. 3B illustrates an operating range over which certain injectors having a set power limit may operate.

In the power limited operating range of another example of the present invention illustrated in FIG. 3B, a minimum pressure of 30 psi at the syringe tip is preferably achieved with an upper pressure limit of 50 psi. The minimum pressure specification is determined by ensuring that the motor (at the power limit) can generate enough force to overcome drive and syringe inefficiencies and losses in addition to 30 psi of fluid pressure. The upper pressure limit specification is met by ensuring that the power delivered to the drive mechanism (for example, motor current) is limited so that the amount of torque generated at the motor output is not large enough to exceed the upper pressure limit of 50 psi at the syringe.

To meet pressure specification, the total equivalent pressure variation in system components, including the syringe, preferably does not exceed ±10 psi assuming a nominal maximum pressure (that is, a power limiting pressure) of 40 psi. Since substantial variation in motor and drive efficiency is expected, some form of calibration may be desirable to relate the motor current limit to actual fluid pressure. Syringe friction in this example is constrained by a product specification to be less than or equal to 7.5 psi. Assuming the syringe friction will vary from 2.5 to 7.5 psi, the calibration method used is preferably accurate enough to set the power limiting pressure of the injector to within ±7.5 psi (10 psi–(7.5 psi–2.5 psi)/2).

The current supplied to the motor is limited to meet the 50 psi maximum pressure specification. The limit value preferably accounts for the different components that make up motor current. At the motor, the motor current can be expressed in equation 1 as follows (as viewed from the motor output shaft):

$$I_A = \frac{1}{K_T} \cdot (J \cdot \alpha_{cmd} + D \cdot \omega_{cmd} + \tau_p + \tau_f) \qquad \text{Equation 1}$$

where $\alpha_{cmd}$ is the commanded acceleration of the motor

D is the viscous damping coefficient for velocity dependent torque losses for the system as viewed from the motor shaft (motor viscous damping plus reflected load damping)

$I_A$ is the motor armature current
J is the inertia at the motor shaft (armature inertia plus reflected inertia)
$K_T$ is the motor torque constant
$\tau_p$ is the portion of motor torque that contributes to pressure in the syringe
$\tau_f$ is the portion of motor torque that is used to overcome motor and system friction losses
$\omega_{cmd}$ is the commanded velocity of the motor The set motor current limit preferably accounts for the components of the motor current that contribute to motor acceleration, motor velocity, and system frictional losses. These components can be accounted for by using design values, or for more accuracy, by characterizing values for a system using a pressure calibration process.

Pressure calibration is particularly desirable in the case of tight pressure specifications. Once again, pressure is limited to the upper pressure limit by limiting the current available to the motor in this example. However, that current goes through several transformations before emerging from the syringe tip as pressure:

Current becomes torque via the motor's torque constant

Torque is magnified through a gear train

Torque becomes linear force via a lead or ball screw

Linear force on the plunger becomes pressure in the syringe

Each of these transformations can contain substantial amounts of variation, for example:

from part to part and/or lot to lot in manufacturing as a function of injector position (or angle)

as a function of syringe velocity as a function of plunger acceleration as a function of temperature as a function of injector use and/or wear (sometimes referred to as "run-in")

A carefully executed calibration procedure, performed once during manufacture, can substantially reduce or eliminate the contributions of part-to-part variation, and variation over velocity and acceleration. This calibration procedure does not account for contributions of the syringe and variations over position, temperature, and life. On a unit-to-unit basis, calibration can also identify units for rejection which exhibit excessive variation over position. Proper motor selection can keep variation over temperature to a manageable level. If variation over life is large systematically, however, periodic auto-calibration is desirable.

In the case that motor current is used to indirectly measure fluid pressure, for example, the drive member can be used occasionally to advance the plunger with no fluid in the syringe to measure the contribution of syringe friction. Periodic auto-calibration in the case of the use of a force sensor or pressure transducer to measure fluid pressure is discussed below.

In general, motor converts current into torque as set forth in equation 2:

$$\tau_g = K_t \cdot I \qquad \text{Equation 2}$$

where $\tau_g$      is the generated torque
$K_t$      is the motor's torque constant
I      is the current drawn by the motor The generated torque is divided as follows in equation 3:

$$\tau_g = J \cdot \alpha + B \cdot \omega + \tau_L \qquad \text{Equation 3}$$

where

J  is the equivalent inertial load at the motor
α  is the acceleration
B  is the equivalent viscous damping (friction) at the motor
ω  is the velocity
$\tau_L$  is the constant opposing torque (friction and losses) at the motor Thus, the motor current goes to three components:

$$I=(J/K_t)\cdot\alpha+(B/K_t)\cdot\omega+(\tau_L/K_t) \qquad \text{Equation 4}$$

Preferably, these three components are characterized at least at the pressure minimums and maximums (30 and 50 psi in this example). To accomplish this characterization, steady-state moves are preferably performed with a known load at different velocities, while measuring the motor current. During these steady-state moves, it can be determined whether or not the variations of the mechanics over position are acceptable. If so, then the data from the different velocities can be fit to a line (or parabola, if the data warrants), yielding the second and third components of equation 4. Subsequently, current measurements are preferably taken during standard accelerations. Given that the current, the second component of equation 4, and third component of equation 4 are known, the first component of equation 4 can be calculated.

Once the above procedure has been performed for both 30 and 50 psi, one can determine current limits for all velocities, and an offset to these limits during accelerations. This determination is preferably made by taking the current limit to be midway between the 30 psi and 50 psi values (adjusting for the syringe variations). Should the 30 and 50 psi current values be too close together, this method will not work properly and the unit should be rejected. The calculated current limits are preferably then stored in memory (for example, non-volatile memory or NVRAM) and used by the injector software during normal operations.

Figure 3C:
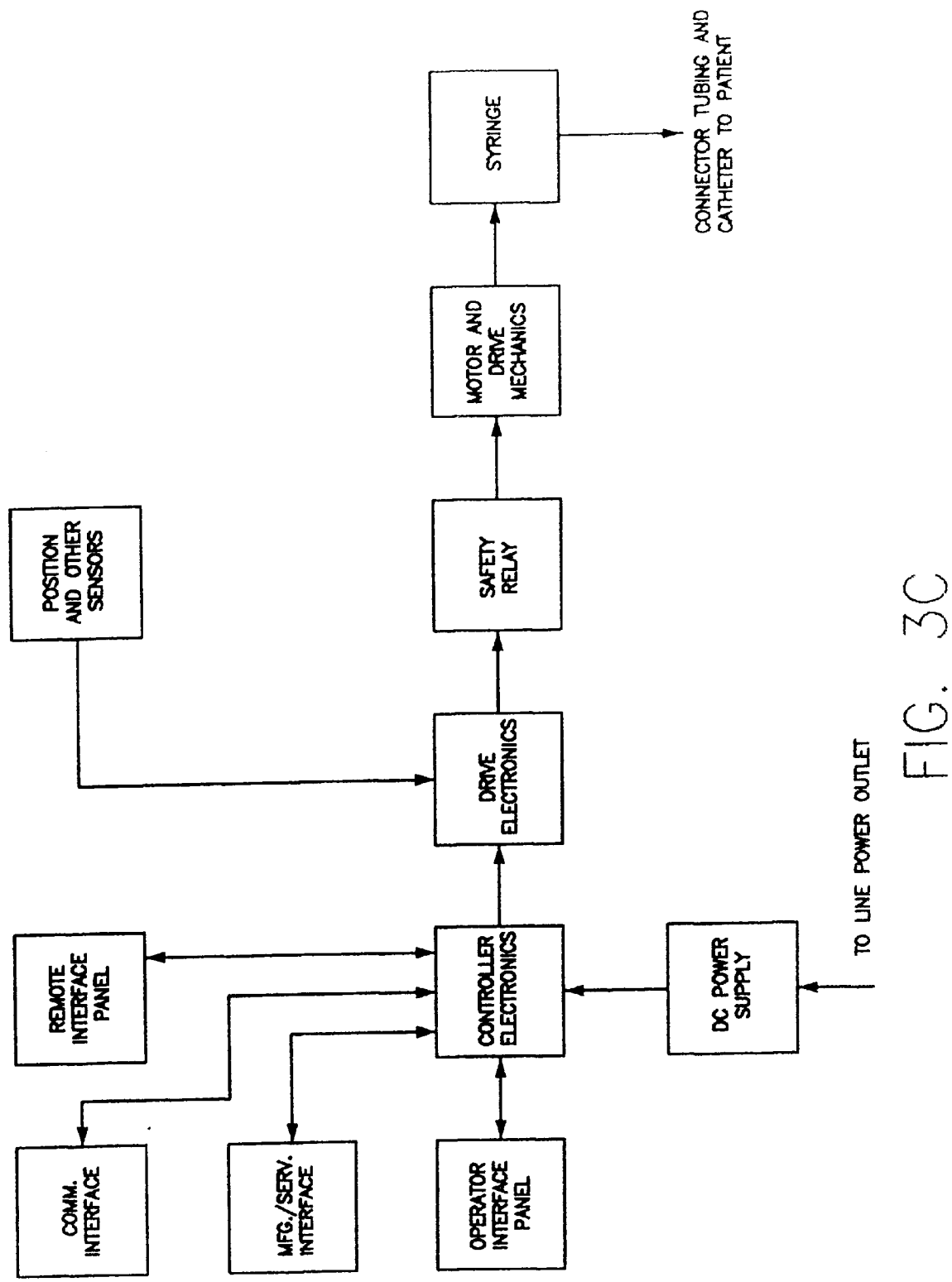
FIG. 3C illustrates a schematic representation of the embodiment of FIG. 1A including a monitoring system for various conditions.

In addition to monitoring for an upper pressure limit as described above, there are several other safety monitor functions that are preferably active during operation of the injector system in the embodiment of FIG. 3C. For example, these functions can monitor for over-rate, under-rate, over-volume, over-pressure and unintended piston motion conditions (fault conditions). In the embodiment of FIG. 3C, these monitors deactivate a safe relay, which has the function to remove power from the drive mechanism (for example, by cutting off current from a motor) in the case of a safety fault condition. The safe relay can, for example, be a mechanical relay, a solid-state relay, or any other device that can be used to interrupt or remove power from the motors or motivation device. in a typical embodiment, the safe relay device is activated by the system to allow power to the motor and when deactivated, either by command or through a fault condition, is deactivated to interrupt or remove power.

An over-pressure circuit can, for example, be a hardware safety circuit or a software component that is designed, for example, to deactivate the safe relay and remove power from the drive to prevent the generation of a hazardous pressure level as described above. The monitor preferably operates by measuring and comparing an average value of the drive power (that is, motor current) and removing power from the drive if it exceeds a maximum threshold level (that is, the motor current corresponding to the pressure hazard limit).

An over-rate monitor circuit preferably includes a safety circuit that is designed to deactivate the safe relay to remove power from the drive to prevent the generation of hazardous flow rates. The monitor operates by measuring the piston position with a position sensor and differentiating to obtain an estimate of piston velocity (flow rate). Alternatively, a velocity sensor such as a tachometer could be used to measure flow rate directly. When compared, if the measured flow rate exceeds a programmed flow rate by a set amount (set by a threshold level) the safe relay is preferably deactivated and power removed from the drive.

In generally the same manner an under-rate or stall condition can be monitored. In the case of under-rate monitoring, the measured flow rate is compared to the programmed flow rate. If the measured flow rate falls below the programmed flow rate by a set amount (set by a threshold level) the safe relay is preferably deactivated and power removed from the drive. A stall condition can be caused, for example, by a blockage in the fluid path, which can be of increased concern when the injector is operating in a power limited state.

An over-volume monitor preferably includes a safety circuit that is designed to deactivate the safe relay to remove power from the drive to prevent excess volume from being administered to a patient. The monitor preferably operates by measuring the piston position and comparing it to a target position based on the programmed flow rate/volume. If the measured piston position exceeds the programmed target position (volume) by more than a set amount, the safe relay is preferably deactivated and power is removed from the drive.

An unintended motion monitor preferably includes a safety circuit that is designed to deactivate the safe relay to remove power from the drive to prevent unintended movement of the piston, which could cause unintended injection or aspiration, when the injector system is supposed to be in an idle state. The monitor preferably operates by monitoring the forward and reverse piston position motion when the injector system is in an idle state. If the net forward or reverse position exceeds a set travel amount, the safe relay is deactivated and power is removed from the drive.

The injector systems of FIGS. 1A through 3C control injection fluid flow until a power limit value is reached. In other words, the injector systems maintain the delivered fluid flow rate to an operator-programmed value or setting providing the required pressure as needed based on the restriction of the fluid delivery path. Once a power limit value is reached, the injector systems deliver whatever flow rate is possible at the power limit until the operator determined fluid volume is delivered, given the pressure generated and disposable set used. In the case of a severe restriction of the fluid path, for example, the achieved flow rate can be significantly below the programmed value and the injection will be terminated (a stall condition). If for any reason the power limit fails and the pressure exceeds a pressure hazard limit, an over pressure monitor detects the condition and stops fluid delivery.

Other embodiments of injector systems of the present invention are illustrated in FIGS. 4A through 5C. In these embodiments of the present invention, pressure measurement is improved by using a more direct measurement thereof than motor current. As illustrated in FIG. 5A, for example, one can measure the force (using, for example, a strain gauge) on the mechanical assembly that supports the drive train or syringe and convert or relate the measured force to fluid pressure. In general, one can measure the force exerted on any injector component that bears a force proportional to the fluid pressure. A sensor can also be positioned to measure the force on the injector piston as illustrated in FIG. 5A. Likewise, actual fluid pressure can be measured via, for example, a pressure transducer or sensor in the fluid path as illustrated in FIG. 5A.

Use of a force sensor in connection with the drive train eliminates most tolerances in the interpretation of pressure measurements other than, for example, those caused by the friction of the plunger moving in the syringe. Use of a fluid pressure senor in the fluid path generally eliminates all tolerances in interpretation. Other methods of measuring fluid pressure suitable for use in the present invention are disclosed, for example, in U.S. Pat. No. 5,808,203, the disclosure of which is incorporated herein by reference.

Figure 5B:
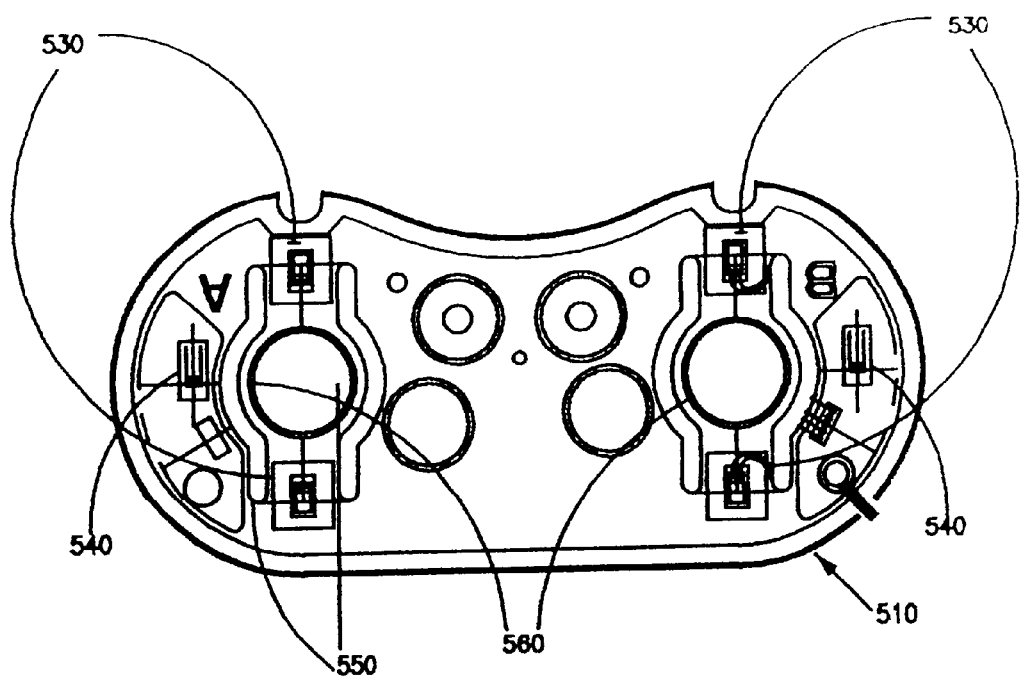
FIG. 5B illustrates a front plan view of a rear plate including strain gauges.
Figure 5C:
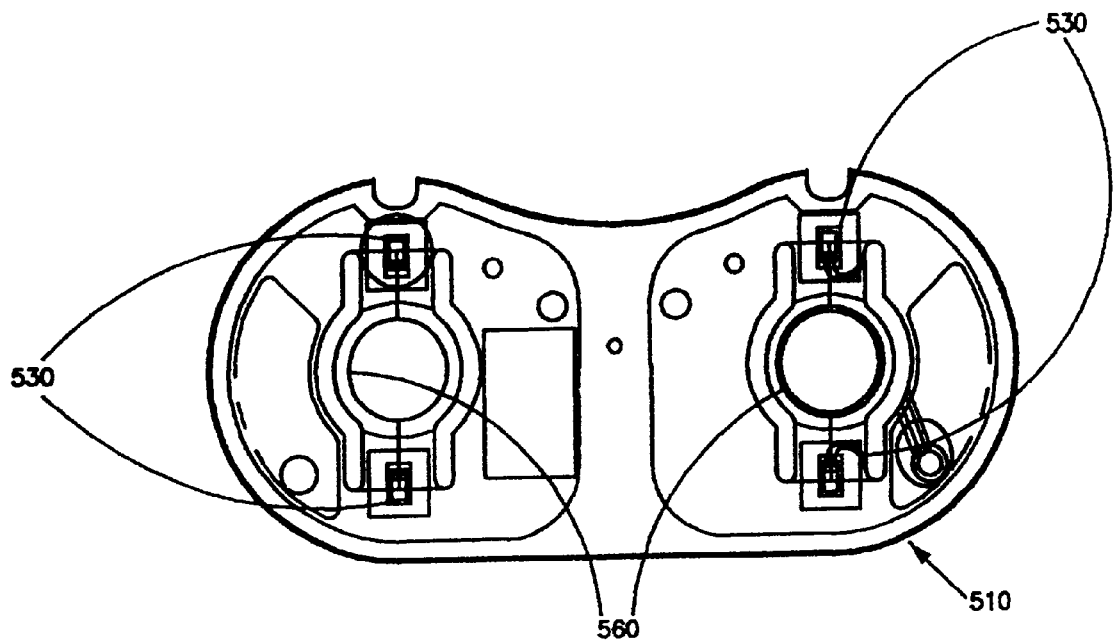
FIG. 5C illustrates a rear plan view of the rear plate of FIG. 5B including strain gauges.

FIGS. 5B and 5C illustrate one aspect of the present invention in which strain gauges 530 are placed in connection with a mechanical drive rear plate 510 of an injector (such as the Spectris injector available from Medrad, Inc. of Indianola, Pa., now shown in FIGS. 5B and 5C), which secures ball screw thrust bearings for each of two pistons inside the injector head housing (not shown). The syringe plungers are driven by these pistons as described above. Rear plate 510 is the primary load bearing plate within the injector head and, therefore, provides a strain response that is directly proportional to syringe pressure. The strain on rear plate 510 can be measured by using the voltage output of strain gages 530 bonded directly to the surface of rear plate 510. This voltage output can be translated to a pressure value.

In the embodiment of FIGS. 5B and 5C, strain gauges 530 are configured as a Wheatstone bridge. There are two full bridges mounted to rear plate 510 with one bridge mounted on the front (syringe) side (FIG. 5B) and one bridge mounted on the rear side (FIG. 5C). Each bridge includes four strain gauges 530, two mounted on the syringe side of the rear plate and two mounted on the rear side (see FIGS. 5B and 5C). Strain gauges 530 function by measuring changing voltage resistance values within each gauge as the strain on the surface of the plate 510 (to which the gauge has been mounted) changes in magnitude. This strain occurs when the piston is under load (such as during an injection) and thus transfers it's stress back to rear plate 510. Reading the output voltage from all four strain gauges 530 simultaneously eliminates any apparent fluctuation within the pressure readings caused by an inherent wobble that occurs while the piston is in motion. In one embodiment, the full-scale voltage of strain gauges 530 corresponded to a strain of 1000 $\mu\epsilon$ (microstrain) at 300 lbs of piston load. Span resistors 540 can be mounted on the syringe side of rear plate 510 to adjust the bridge output so that one transducer bridge produced a similar output to another bridge mounted onto a different plate 510.

In the embodiment of FIGS. 5B and 5C, strain gauges 530 and span resistors 540 were bonded to rear plate 510 using an epoxy. Prior to bonding, a surface preparation process as known in the art was performed to provide an adequate bonding surface for the epoxy. The material selected for the rear plate construction was Aluminum 2024-T351. Strain gauges 530 were J2A-13-S033P-350 strain gauges available from Measurements Group, Inc of Raleigh, N.C. Strain gauges 530 were attached to rear plate 510 using M-Bond 610 epoxy available from Measurements Group, Inc. Once strain gauges 530 were bonded to rear plate 510, they were coated with GageKote #8 (an acrylic compound that creates a transparent coating between 5–10 mils thick per coat), available from JP Technologies Inc. of San Bernadino, Calif., to anchor the wiring directly to rear plate 510.

For strain gauges 530 of the above embodiment, the strain level preferably does not exceed 1000 $\mu\epsilon$ at the area where strain gauges 530 were mounted to rear plate 510. To achieve an output from strain gauges 530 that produced a maximum output and resolution, rear plate 510 was designed such that strain gauges 530 experience 1000 $\mu\epsilon$ at a maximum expected cyclic load condition at 300 lbs of piston load. The maximum expected static load on rear plate 510 was 450 lbs, which translated to 1500 $\mu\epsilon$ at the area where strain gauge 530 was mounted. To achieve the above-mentioned levels of strain, channels 550 were machined in a pattern around the main bearing areas 560 to produce a symmetrical load condition about the bearing. Creation of a strain area allowed ready adjustment (using, for example, finite element analysis) of the geometry until the optimal strain levels were achieved. In this embodiment, strain gauges 530 were placed as shown in FIGS. 5B and 5C on both the front and back of rear plate 510. The symmetrical constraints of the beams allow for piston wobble, which can increase and decrease the load in an equal and opposite manner from one beam to the other, essentially averaging the strains so that there is a stable bridge output.

Figure 4A:
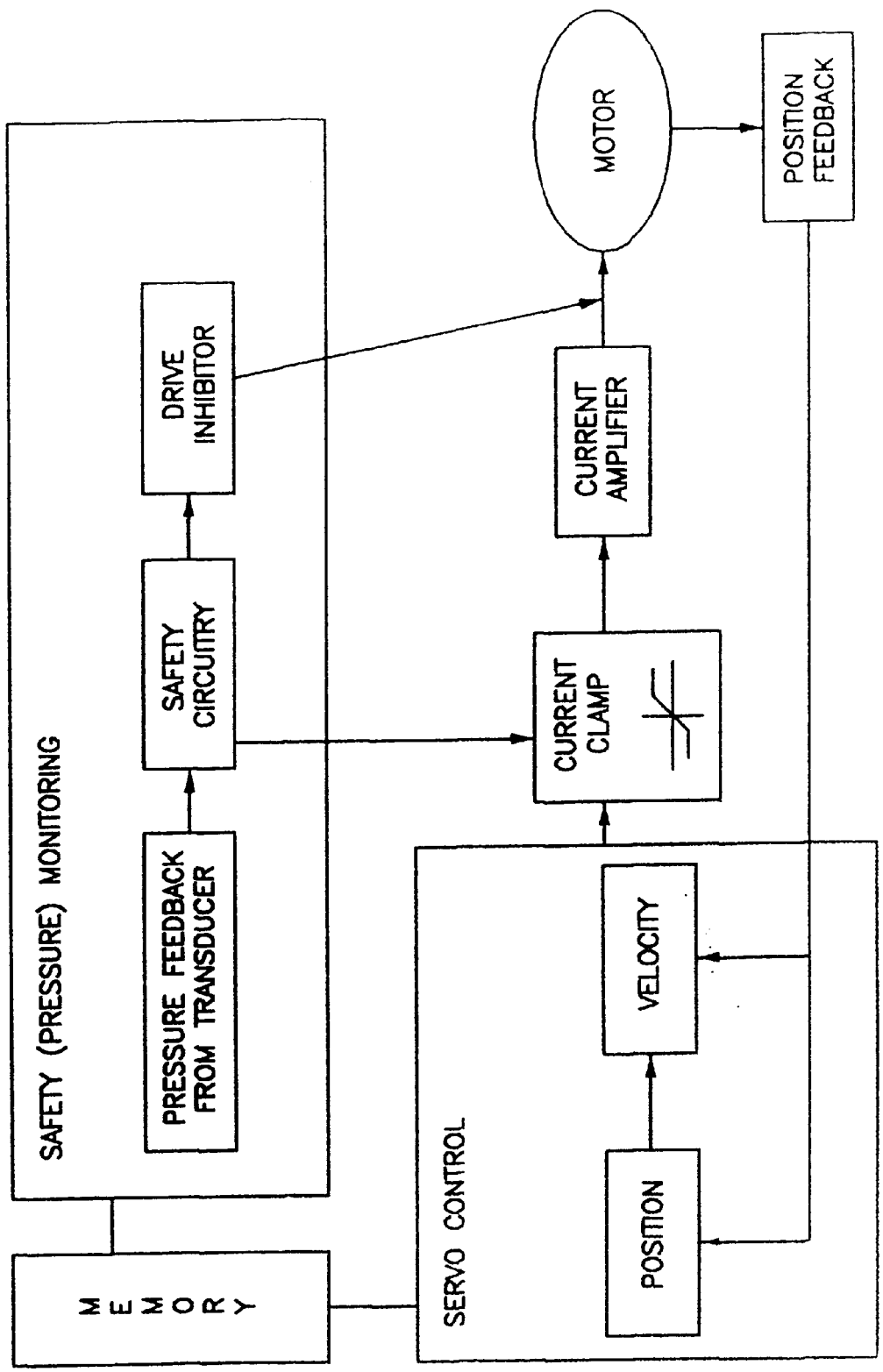
FIG. 4A illustrates a schematic representation of an embodiment of an injector system of the present invention in which a force sensor or transducer is used to measure pressure.

In the embodiments of FIGS. 4A through 5C, the servo controlling fluid flow rate and volume of fluid delivered can be generally separate in operation from a safety (pressure) monitoring system. The servo controls generally only the flow rate of the fluid and the volume of the fluid delivered. Unlike the embodiment of FIGS. 1 through 3C, there is no motor current feedback control loop within the servo control. Fluid flow rate and volume are directly related to the velocity and position of the drive member, respectively, and can be controlled, for example, through feedback of position as illustrated in FIGS. 4A and 4B.

Figure 4B:
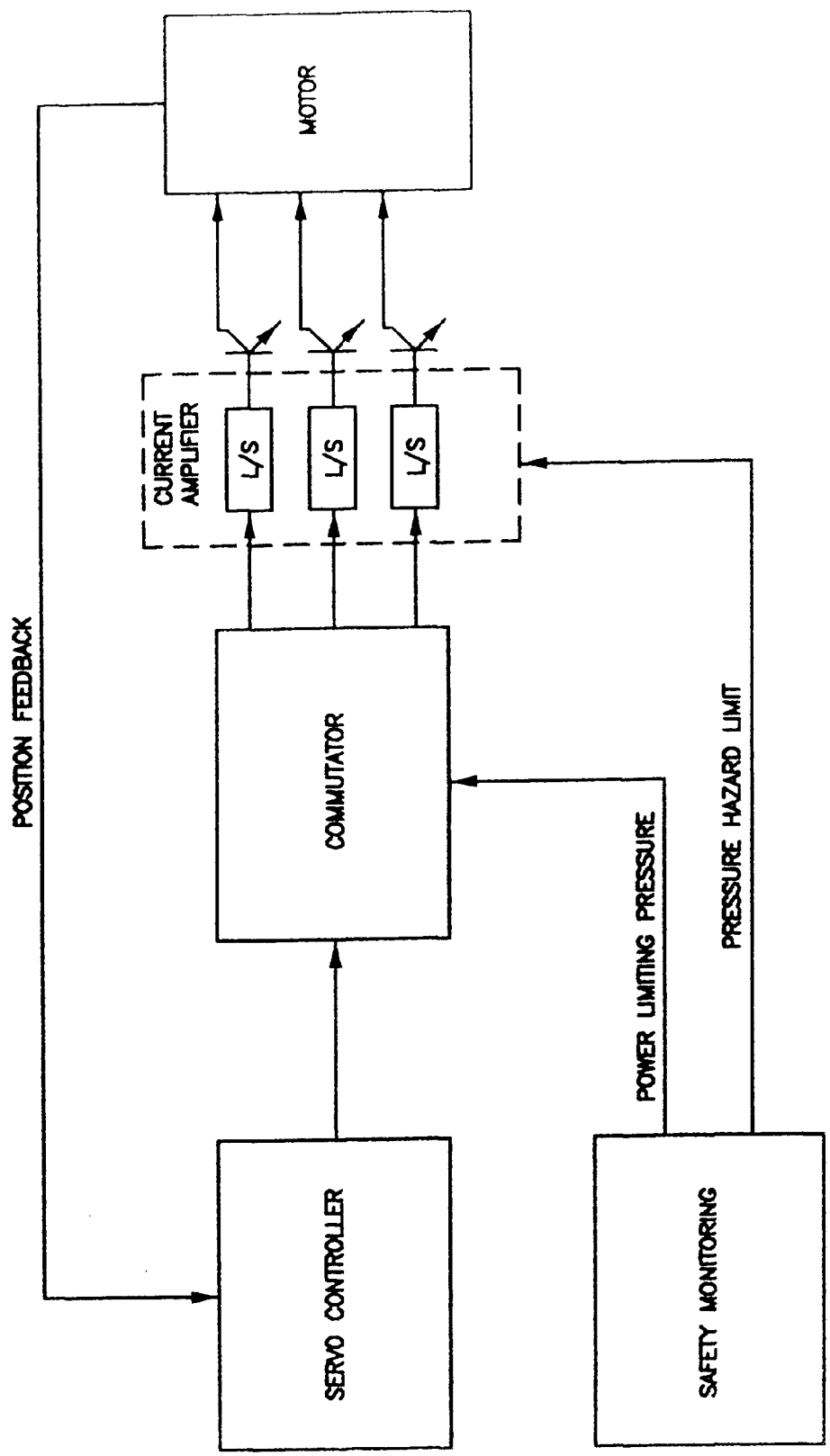
FIG. 4B illustrates a schematic representation of an embodiment of the injector system of FIG. 4A.
Figure 4C:
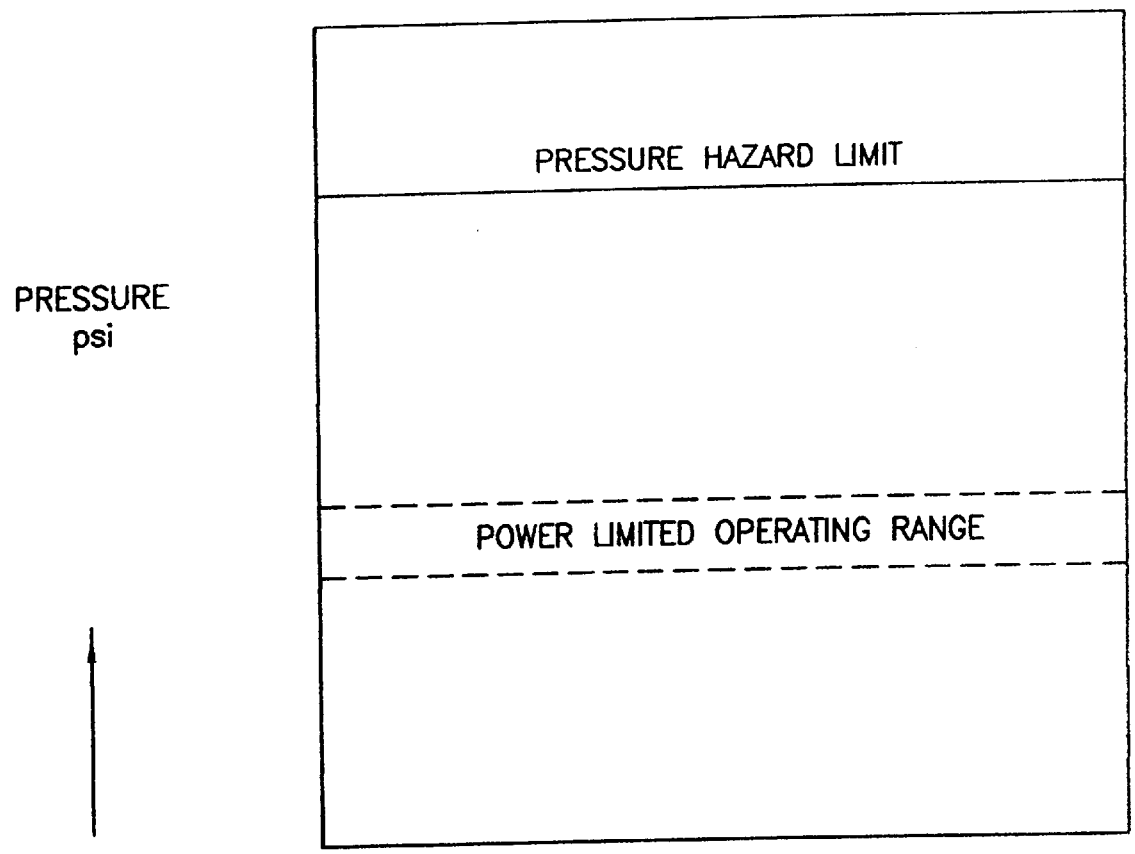
FIG. 4C illustrates a power limited operating range of the injector systems of FIGS. 4A and 4B.

As illustrated in FIG. 4C a pressure hazard limit is preferably set at a level to prevent, for example, failure (or bursting) of any component of the fluid path or disposable set. Once the pressure hazard limit is reached, as determined by the pressure monitoring system, an injection procedure is preferably ceased, for example, by preventing current from reaching the motor. In one embodiment, a non-mechanical drive inhibitor is provided that inhibits or disables drive circuits that that are in operative connection with power transducers that act as current amplifiers to power the motor. The drive inhibitor generally performs the functions of the mechanical safe relay discussed in connection with FIGS. 1 through 3C in this embodiment. In general, mechanical embodiments of safe relays are expensive and include magnetic components the can malfunction and/or create artifacts in magnetic resonance environments.

A pressure that is lower than the pressure hazard limit is preferably chosen/identified at which the injector system becomes power limited. For example, current delivered to the motor can be clamped via a current clamp as described above once the power limit pressure is measured. With data/feedback from a real time force sensor or pressure transducer available to the injector system, it is not necessary to preset the power limit before the injection begins (as done in the embodiment of FIGS. 1A through 3C). The power limit can, for example, be activated in real time during an injection procedure by monitoring the force sensor or transducer and setting the power limit (for example, by setting maximum motor current) when the measured force reaches a value corresponding to the power limiting pressure.

FIG. 4B illustrates another embodiment of an injector system of the present invention in which a servo controller controls only fluid flow rate and volume via position feedback as described above. In general, the servo controller sends a signal to a commutator that, in turn, transmits timed signals to a current amplifier including a plurality of level shifters (L/S) or power transducer. In general, the commutator energizes the level shifters in sequence, each for a specific amount of time. The amount of time each level shifter is energized controls the motor power. Separate from the servo controller, a safety (pressure) monitoring system monitors the fluid pressure via a force sensor as described above. In this embodiment, if the safety monitoring system detects that the power limiting pressure has been reached, a signal is sent to the commutator that sets a power clamp as described above by limiting the amount of time the level shifters are energized. If the safety monitoring system detects that the hazard pressure limit has been reached, a signal is sent to the current amplifier that disables the level shifters, thereby stopping the injection procedure. In such an embodiment of the present invention, the servo controller and the safety monitoring system act independently. The safety monitoring system can be viewed as a safety or pressure override system in that the settings programmed into the servo controller by the system operator can be overridden by the safety monitoring system upon the measurement of the power limiting pressure or the pressure hazard limit.

Setting the power limit during operation of the injector eliminates variances caused by temperature and equipment wear, and essentially recalibrates the system during every injection, allowing even more accurate setting of the power limit point. Periodic pressure measurement recalibration can, for example, be performed by measuring force when the system is in a known state (for example, it is known that a syringe is not attached). The system can determine the difference between the measured force and the force that is reasonably expected to be measured when the system is in the known state, and can recalibrate the force sensing system accordingly.

Because the system is effectively recalibrated during every power-limited injection, the injector also has the capability to "learn" from past trends. For example, software algorithms, as known in the computer arts, can use information recorded in memory to learn the behavior of the system and adjust for expected performance changes based on those trends. Calibration changes can, for example, be predicted.

In the injector systems of FIGS. 4A and 4B, the pressure monitoring system determines if the power limiting pressure has been reached and the current/power is clamped at that point. The improved pressure measurement in the embodiment of FIGS. 4A and 4B as compared to deriving fluid pressure from motor current results in a narrowed power limited operating range. As discussed above, the more direct measurement of pressure greatly reduces or eliminates the uncertainty resulting from tolerances of the injector system.

Although sensing pressure via a force transducer on mechanical members of the drive train is superior to the use of motor current, tolerances in the system remain (the largest of which is plunger friction against the syringe barrel) that cause operation to vary within the power limiting performance range illustrated in FIG. 4C. In general, for the injector system to provide the required performance, the lower pressure limit of that range preferably allows sufficient power to deliver fluid per the specifications of the system. There is also a practical constraint on the upper pressure limit of the range in that it should not reach the pressure hazard limit level. If the upper limit of the power limited range overlaps the pressure hazard limit, the injector system can periodically shut down under normal operating conditions and inconvenience the user. A gap between the upper limit of the power limited range and the pressure hazard limit assists in preventing such nuisance shutdowns. The greater tolerances involved in using motor current to measure pressure render it difficult to achieve the proper balance without setting the pressure hazard limit level to an undesirably high level.

To determine an appropriate power limited range, a system simulation model which modeled components of variation within the system was used. In several studies, a Monte Carlo analysis yielded power requirements for each of several planned injection fluids (contrast agents), for each of several planned disposable fluid paths setups. The resulting values were used to establish a nominal power required for each disposable setup, defined as the Power Limit Target. Based on the variation in the components of the system, such as syringe diameter variation, contrast fluid viscosity variation, etc., a figure for uncertainty was calculated. This uncertainty figure, or sigma, was used as a measure of the distribution (nominal 3 sigma, based on a normal distribution) of expected system performance about the Power Limit Target. This resulted in a family of power limit ranges which can, for example, be software selected for the appropriate disposable setup. The disposable components of a disposable set can, for example, include a syringe and the fluid path (for example, connecting tubing etc.) between the syringe and the patient as described above.

The pressure monitoring systems of FIGS. 4A through 5B also facilitate adjustment of the pressure hazard limit and/or the power limiting pressure by the operator of the injector system. Preferably, however, the pressure hazard limit and the power limiting pressure are related (for example, mathematically coupled in software) such that a sufficient gap is maintained between the pressure hazard limit and the power limiting pressure to substantially reduce the likelihood of nuisance shutdowns of the injector system.

In general, the injector systems of FIGS. 4A through 5C control fluid flow until a power limit pressure is measured. The injector systems maintain the delivered fluid flow rate to an operator-programmed value, providing the required pressure as needed based, for example, on the disposable set in place. Once the power limit pressure is measured (for example, for a defined period of time), the system clamps the power delivered to the motor at that point and delivers whatever flow rate is possible at that power limit. If the flow rate achieved is significantly below the programmed value (for example, less than or equal to 10% of the programmed flow rate as averaged over 3 minutes in the ml/min range or as averaged over 3 seconds in the ml/s range), the injection is preferably terminated and the injector disarmed (a stall condition). If for some reason the power limit fails and the measured pressure exceeds a pressure hazard limit (for example, for a defined period of time), fluid delivery is preferably stopped and the injector disarmed.

Figure 4D:
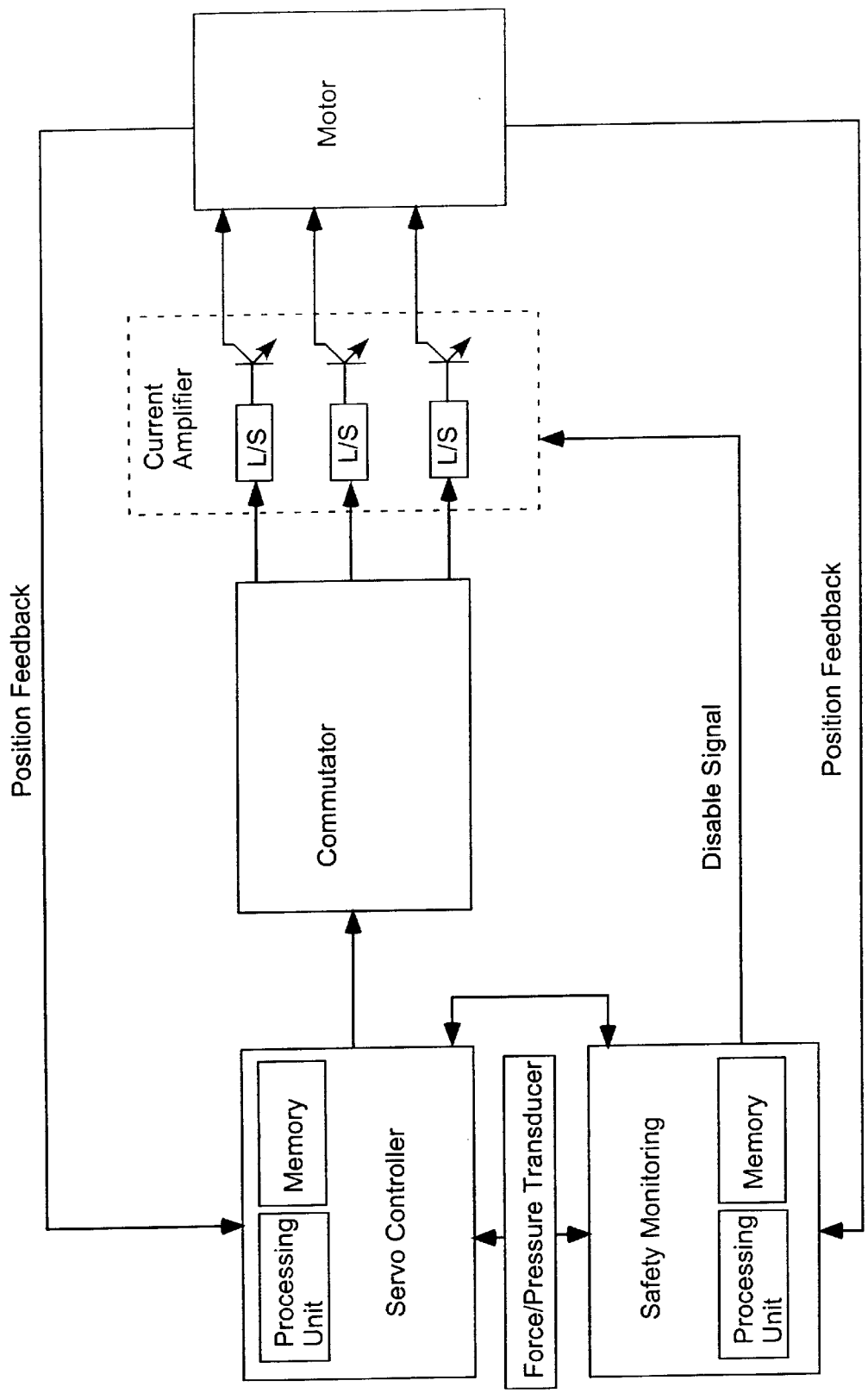
FIG. 4D illustrates a schematic representation of another embodiment of an injector system of the present invention in which a force sensor or transducer is used to measure pressure.
Figure 4E:
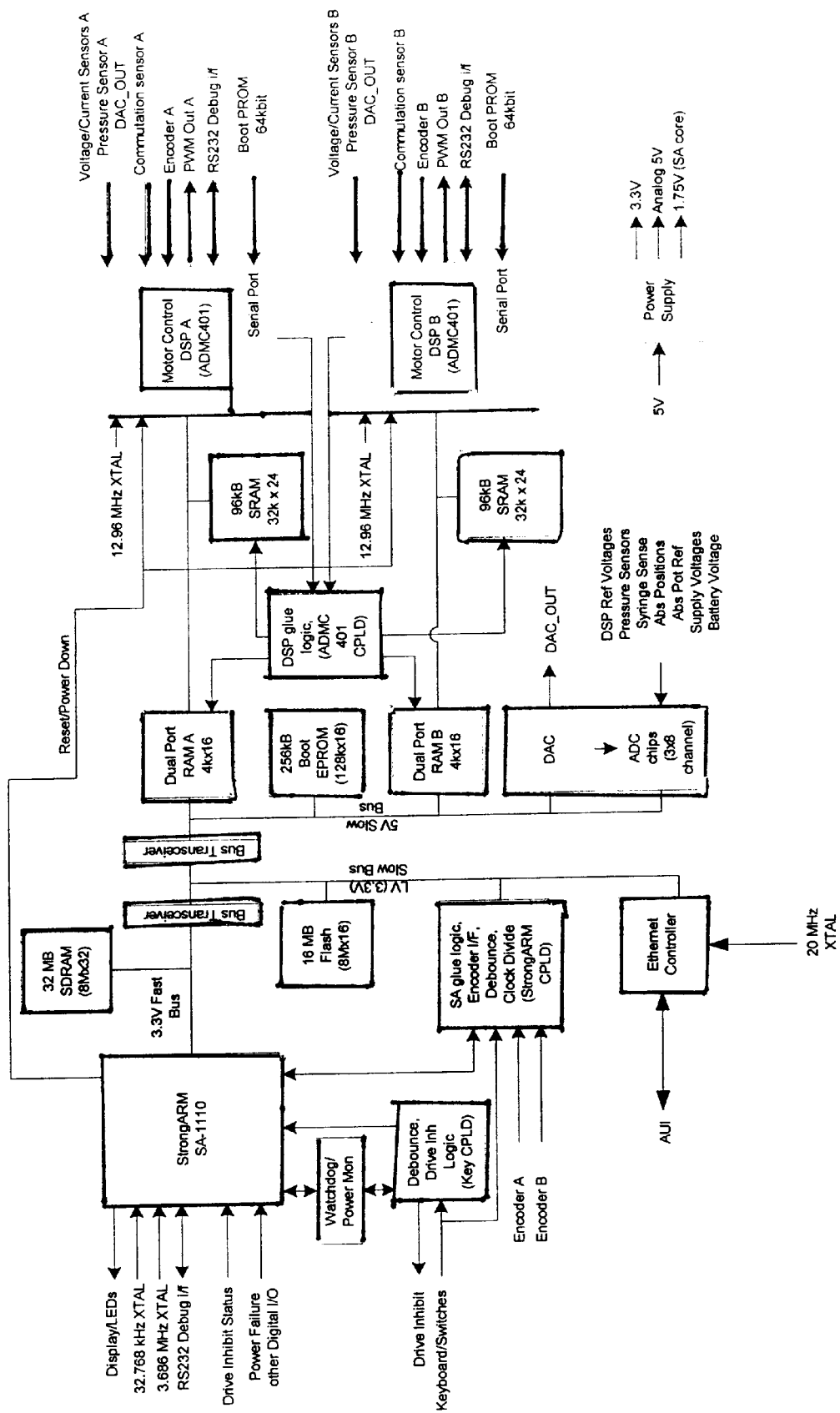
FIG. 4E illustrates a schematic representation of one embodiment of an architecture of the servo controller and safety monitoring system of the present invention.

In the embodiments of FIGS. 4A and 4B, the safety monitoring system clamps the power delivered to the motor as described above. In the embodiment of FIG. 4D, the servo control system performs the actual clamping and notifies the safety monitoring system that it has done so. In this embodiment, the force/pressure transducer can, for example, provide pressure measurement data (for example, every millisecond) to each of the servo controller and the safety monitoring system. The safety monitoring system preferably sets values for both the pressure limiting pressure and the pressure hazard limit. A comparator in the servo controller (for example, embedded in software in a memory in communication with the servo controller's processing unit) monitors the pressure data and compares the measured pressure to the pressure power limiting pressure communicated by the safety monitoring system (which can for example, includes a processing unit in communication with memory).

Once the servo controller clamps the power to the motor, the safety monitoring system in one embodiment attempts to reduce pressure by communicating instructions to the servo controller to gradually reduce flow rate until the pressure reaches some pre-determined "release" value that is lower than the power limiting pressure. For example, if the operator-programmed flow rate is less than 1 ml/s, the flow rate can be reduced by 10%; otherwise, the flow rate can be reduced by 0.1 ml/s. The servo controller delivers the commanded flow rate, while the safety monitoring system continues to monitor the pressure. If, after a reduction in flow rate, the monitored pressure becomes equal to the release value, the safety monitoring system commands the servo controller to release itself from power limiting mode and deliver fluid at a new flow rate determined by the safety monitoring system. This new flow rate can, for example, be set to deliver the original operator-programmed volume, extending the time of injection if necessary. If the monitored pressure has not reached the release value after the first reduction in flow rate, the safety monitoring system continues to send instructions to the servo controller to periodically reduce the flow rate by the above described values until the monitored pressure decreases to the release value. If at any time the resulting flow rate is significantly below the original operator-programmed value (for example, as described above), the injection is preferably terminated and the injector disarmed (a stall condition).

If for any reason the power limiting procedure described above fails, and the measured pressure exceeds the pressure hazard limit (for example, for a defined period of time), fluid delivery is preferably stopped and the injector is disarmed. In the embodiment of FIG. 4D, when monitored pressure reaches the pressure hazard limit, the safety monitoring system issues a command to the servo controller, instructing the servo controller to bring the motor driving the piston to a stop as quickly as possible. The servo controller preferably sets its commanded position parameter equal to its actual position, and its commanded velocity equal to zero. This command causes an immediate deceleration of the motor to zero velocity, at a rate solely determined by the electrical characteristics of the servo control system. Inertia of the motor tends to cause the piston position to keep advancing in a forward direction. The motor is preferably, however, under 4-quadrant control as known in the control arts. In 4-quadrant control, speed control is maintained whether accelerating or braking in both the clockwise and counter-clockwise directions. Thus, even though the motor may be moving forward, PWM cycling is occurring in reverse to "actively brake" the motor until it comes to rest.

Until the motor stops, the commanded position is preferably not modified. The set command position causes the servo controller to resist movement in either direction. When the inertia of the motor is overcome by the servo controller, the actual position of the system will be forward of the command position and, unless the command position is changed, the system will reverse direction to compensate for the disturbance. When this direction reversal is detected by the servo controller, the commanded position is preferably once again set equal to the actual position. This resetting of the commanded position prohibits the servo controller from attempting to pull the motor back to the original commanded position, thus preventing piston retraction (and the possible drawing of blood if connected to a patient). A position hold is then commanded, followed by a motor drive disable command from, for example the safety monitoring system (via a signal to the current amplifier that disables the level shifters as described above) to turn the motor off.

Commercially available servo controllers typically provide very fast processing speeds. Providing pressure measurements directly to the servo controller, with instructions from the safety monitoring system and override control in the safety monitoring system, can quite economically provide swift and safe system control. For example, it has surprisingly been found that, as a result of motor inertia, pressure increases quite rapidly in an injector system with, for example, a blockage in a fluid path even after current is completely removed from the motor. Pressure can, for example, increase at a rate of approximately 1 psi/millisecond. Under such conditions, the pressure hazard limit can be quickly exceeded, giving rise to the possibility of catastrophic failure of, for example, a syringe or a disposable tubing set. Providing 4-quadrant control in the servo controller as discussed above substantially eliminates the risk of substantially exceeding of overshooting the pressure hazard limit.

In one embodiment of the present invention, a digital pressure level signal was provided to the safety monitoring system and the servo controller using an ADC10158CIWM Analog to Digital Converter (ADC) available from National Semiconductor of Santa Clara, Calif. A StrongARM SA-1110 processor available from Intel Corporation of Santa Clara, Calif. was used as the processing unit in the safety monitoring system. A Xilinx XCR3256XL-12TQ144C Coolrunner Complex Programmable Logic Device (CPLD) available from Xilinx, Inc. of San Jose, Calif. was used for related logic. Two Cypress CY7C024-25 Dual Port Memory units were used as an interface between the safety monitor system and the servo controller system. The digital signal processors (DSP) used in the servo controller were ADMC401 DSPs available from Analog Devices of Norwood, Mass. Related logic was provided via a Xilinx XC9536XL-5VQ64C Complex Programmable Logic Device (CPLD). A Xilinx XC9572XL-10VQ64C Complex Programmable Logic Device (CPLD) was used to provide redundant and safety related logic. Communications were provided via a model number LAN91C96 Ethernet controller available from Standard Microsystems. The above components were incorporated in circuit board product number CCAA-002360-03 by Amirix Systems, Inc. of Halifax, Nova Scotia having the general architecture set forth in FIG. 4E.

The injector systems of the present invention thus, as a first priority, preferably deliver the volume of fluid programmed by the operator. As a second priority, the flow rate programmed by the operator is preferably achieved, as long as the measured fluid pressure developed within the injector system is less than the power limiting pressure. The injection is ceased when the programmed volume of fluid has been delivered. If, for any reason, the programmed flow rate is not achieved, the time of the injection is extended to deliver the programmed volume. Under proper operation of the injector system, the power generated by the injector is reduced by the system to keep the operation safe at an internal pressure lower than the pressure hazard limit. The effect of such power limiting is to limit the flow rate that can be achieved with a given disposable set and injection fluid.

In addition to concerns over control of injector systems, it is important to maximize the ease of use of an injector system. In general, current injectors include a housing that encompasses the control and drive mechanisms for the injector. The housing typically also includes a syringe interface to which a syringe can be connected. Such injector housings are often connected to a mobile stand to facilitated positioning of the injector housing. Many such, injector housings are also made to be rotatable about an axis to, for example, further facilitate positioning. Moreover, rotation of the injector housing also enables a syringe connected thereto to be directed upwards to expel air from the syringe (by advancing the syringe plunger in a forward direction). Moreover, rotating the syringe downward during an injection procedure minimizes the risk of injecting air. Although current injector systems do provide some mobility as described above, this mobility is quite limited.

In another aspect of the present invention, at least one syringe interface module is made to be separately movable from the remainder of the injector system. The syringe interface module includes one or more syringe interfaces on a housing thereof for connecting one or more syringes thereto. The syringe interface module also includes at least one drive member (for example, piston) housed therein that is adapted to pressurize fluid within the syringe. The syringe interface module can also include a drive mechanism such as a motor to supply power to the drive member. The drive mechanism can also be remote from the syringe interface module, but in operative connection with the drive member. For example, an electric motor can be connected to the drive member remotely via a flexible shaft. Suitable flexible shafts are disclosed, for example, in U.S. Pat. No. 5,494,036, the disclosure of which is incorporated herein by reference. The separately movable syringe module of the present invention greatly improves the ease of use of the injector systems of the present invention by, for example, expanding the locations/positions in which the injector system can be used.

Figure 6A:
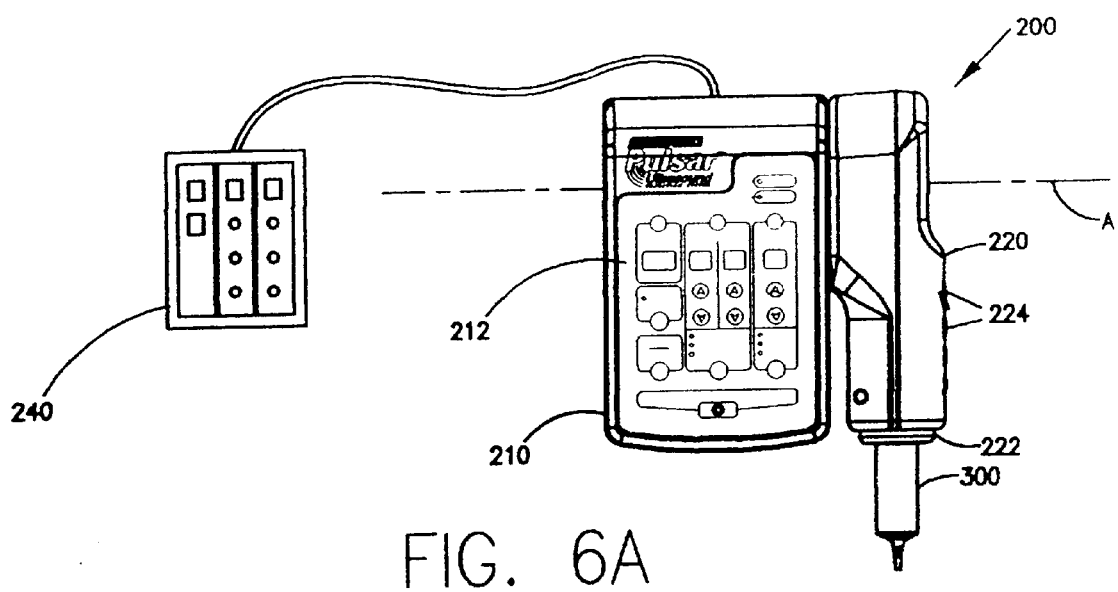
FIGS. 6A through 6C illustrate another embodiment of an injector of the present invention in which an syringe interface module is movable/rotatable relative to a control unit of the injector.

In the embodiment of FIGS. 6A through 5C, for example, an injector system 200 includes an injector having a control unit 210, a syringe interface module 220 and a syringe 300. Syringe interface module 220 includes an interface 222 for connecting syringe 300 thereto. Syringe interface module 220 also houses a powered drive member or piston that controls movement of a syringe plunger 310 (see FIG. 5A). Syringe interface module 220 also houses a motor (see FIG. 5A) in operative connection with the piston. The motor is in communicative connection with control circuitry housed in control unit 210 to supply the motor with control signals as known in the art. Current can also be supplied to the motor via control unit 210. However, syringe injection module 220 can also include an independent power source such as a battery (not shown). Preferably, a portable injector stand 400 supports control unit 210 of injector system 200. Injector system 200 can also include a remote control panel 240 that is in communication with control unit 210. Control switches 212 are preferably used to program control parameters for an injection procedure. Some or all of control switches 212 can be duplicated on remote control panel 240. A number of switches 224 can also be provided on syringe interface module 220 to manually control motion of the drive member (for example, forward, reverse, stop etc.).

Figure 6B:
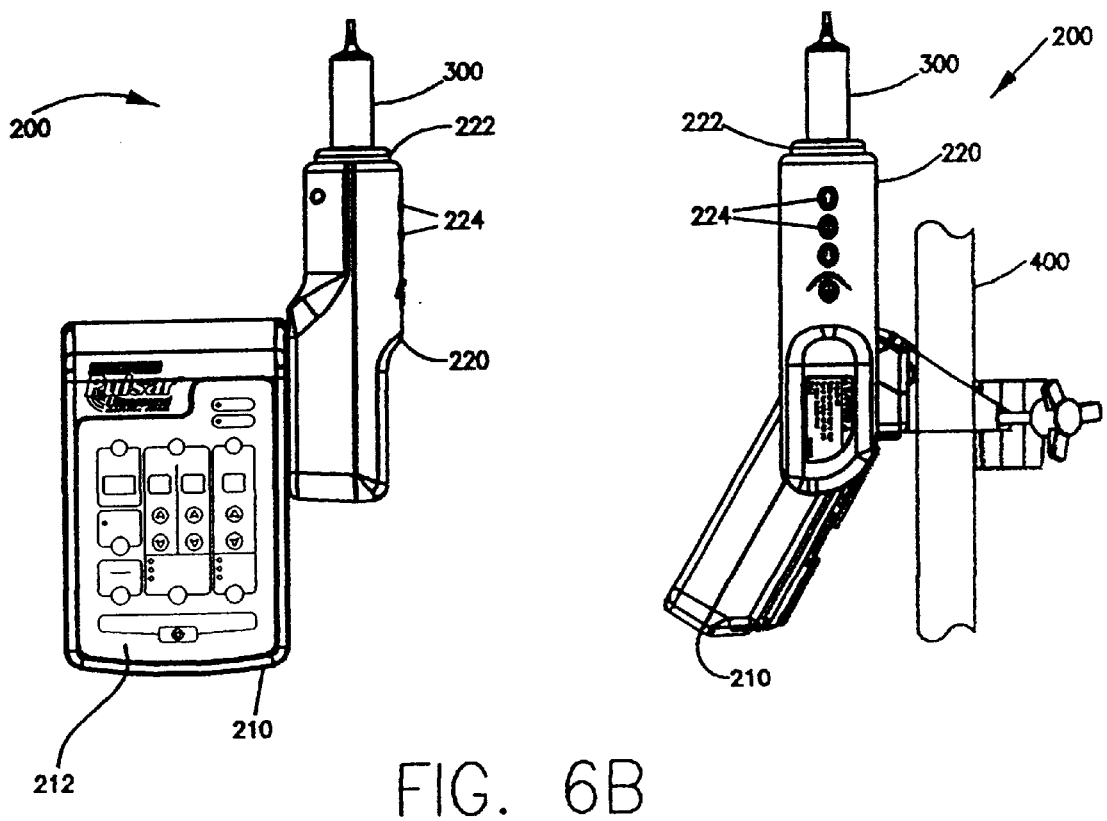
Figure 6C:
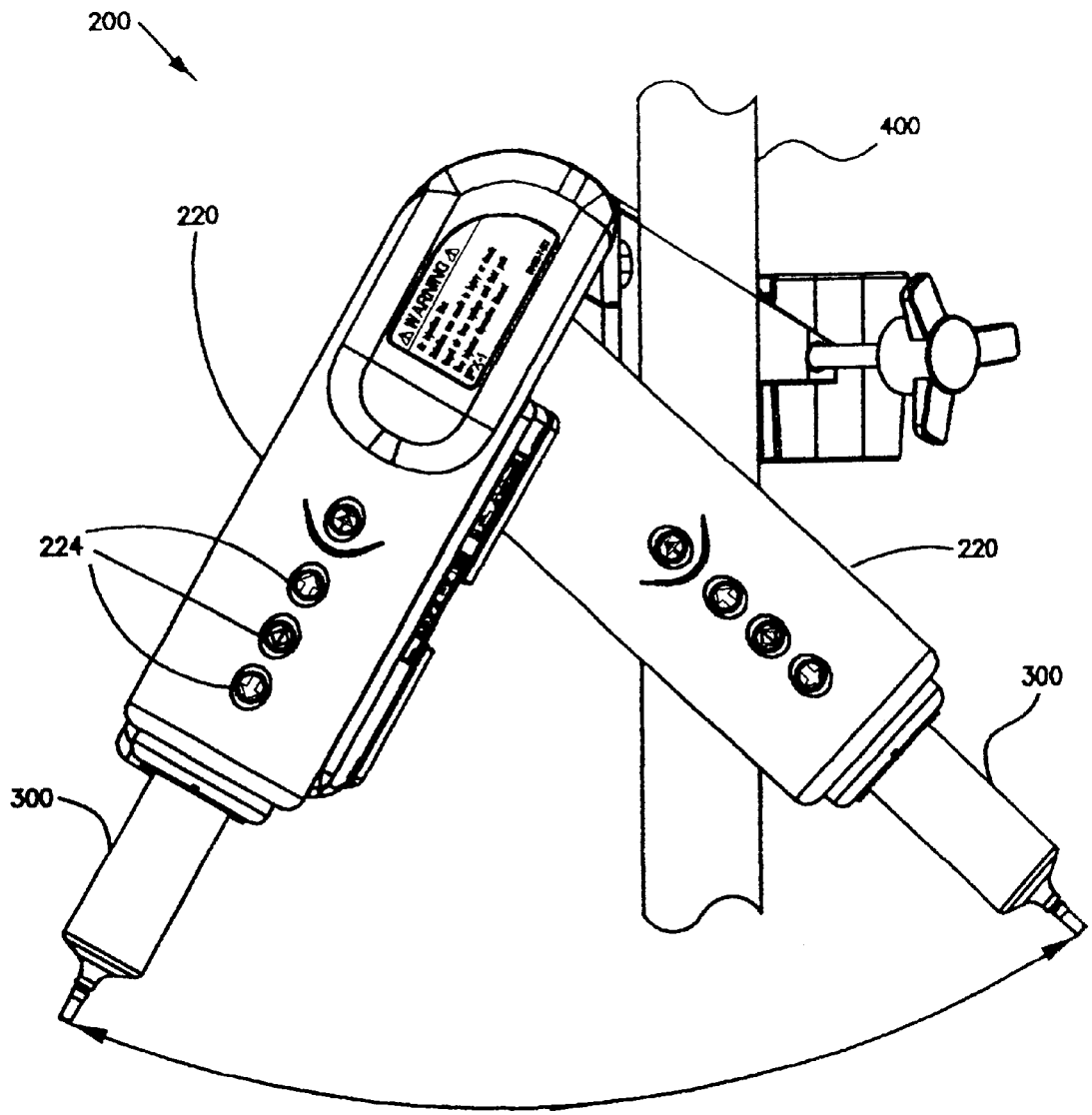
Figure 6D:
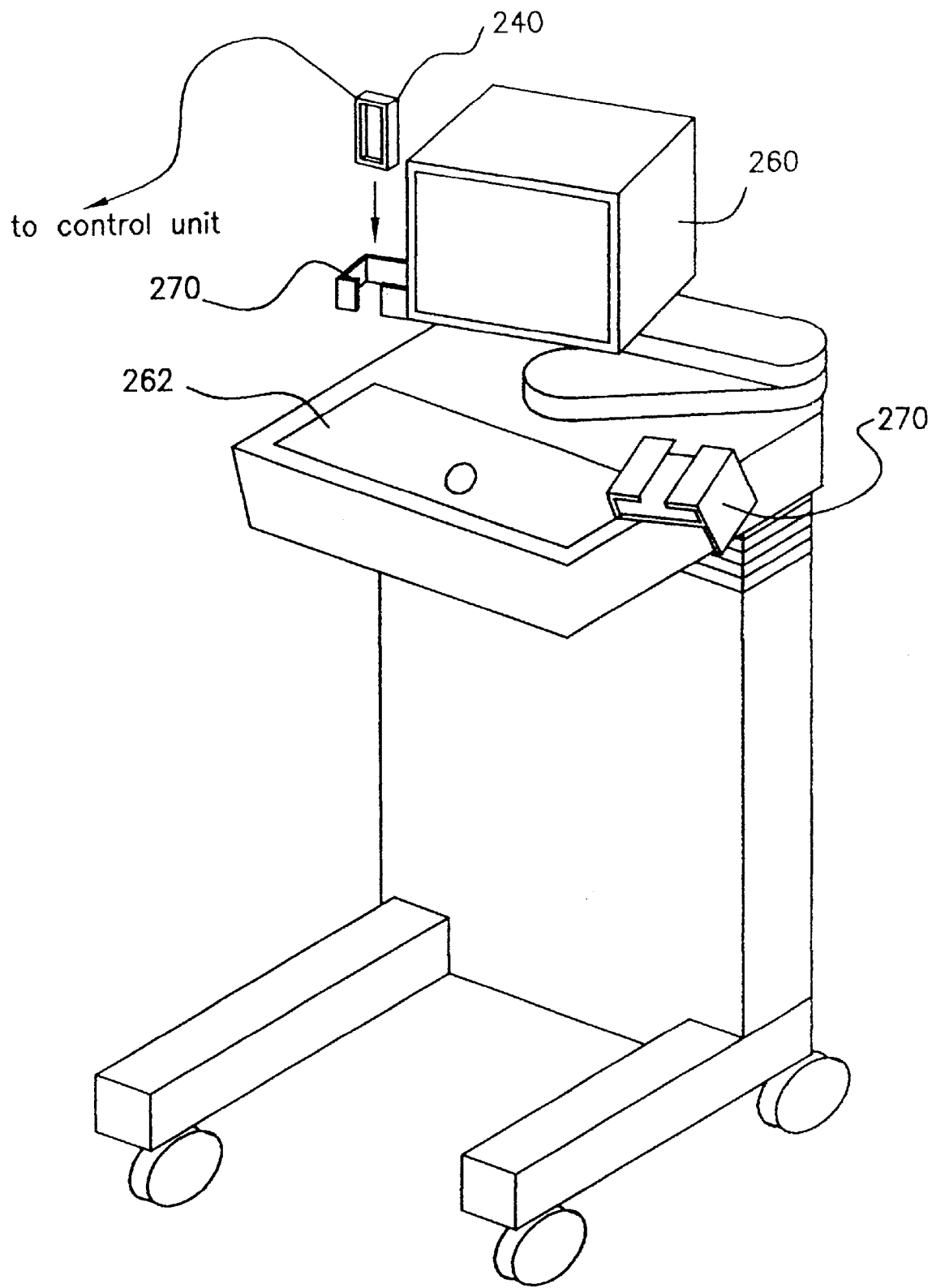
FIG. 6D illustrates an embodiment of a system of the present invention in which an imaging unit is provided with a connector for attaching an injector remote control panel to the imaging unit.

FIG. 6D illustrates an embodiment of a system for carrying out a medical imaging procedure including an imaging apparatus 260 having an input device 262 (for example, a keyboard). The system preferably further includes one or more attachment members 270 for attaching and/or holding remote control panel 240 in the vicinity the imaging apparatus so that an operator can more readily operate both the imaging apparatus and the injector generally simultaneously.

Syringe interface module 220 is rotatable relative to control unit 210 about an axis A. Because syringe interface module 220 is rotatable relative to control unit 210, syringe loading and multiple injection positions are facilitated while providing the operator with easy and consistent access to control switches 212 of control unit 210. The use of injector system 200 in different positions/locations is also facilitated.

FIG. 6B illustrates syringe interface module 220 in an upright position in both a front view and a side view. After injection fluid is aspirated into syringe 300 by retracting plunger 310, air is preferably expelled while syringe interface module 220 is in an upright position. After air is expelled from syringe 300, syringe interface module 220 is rotated downward as illustrated in FIG. 6A (front view) and 6C (side view) for injection. FIG. 6C illustrates an example of a range of injection positions for syringe interface module 220.

Figure 7:
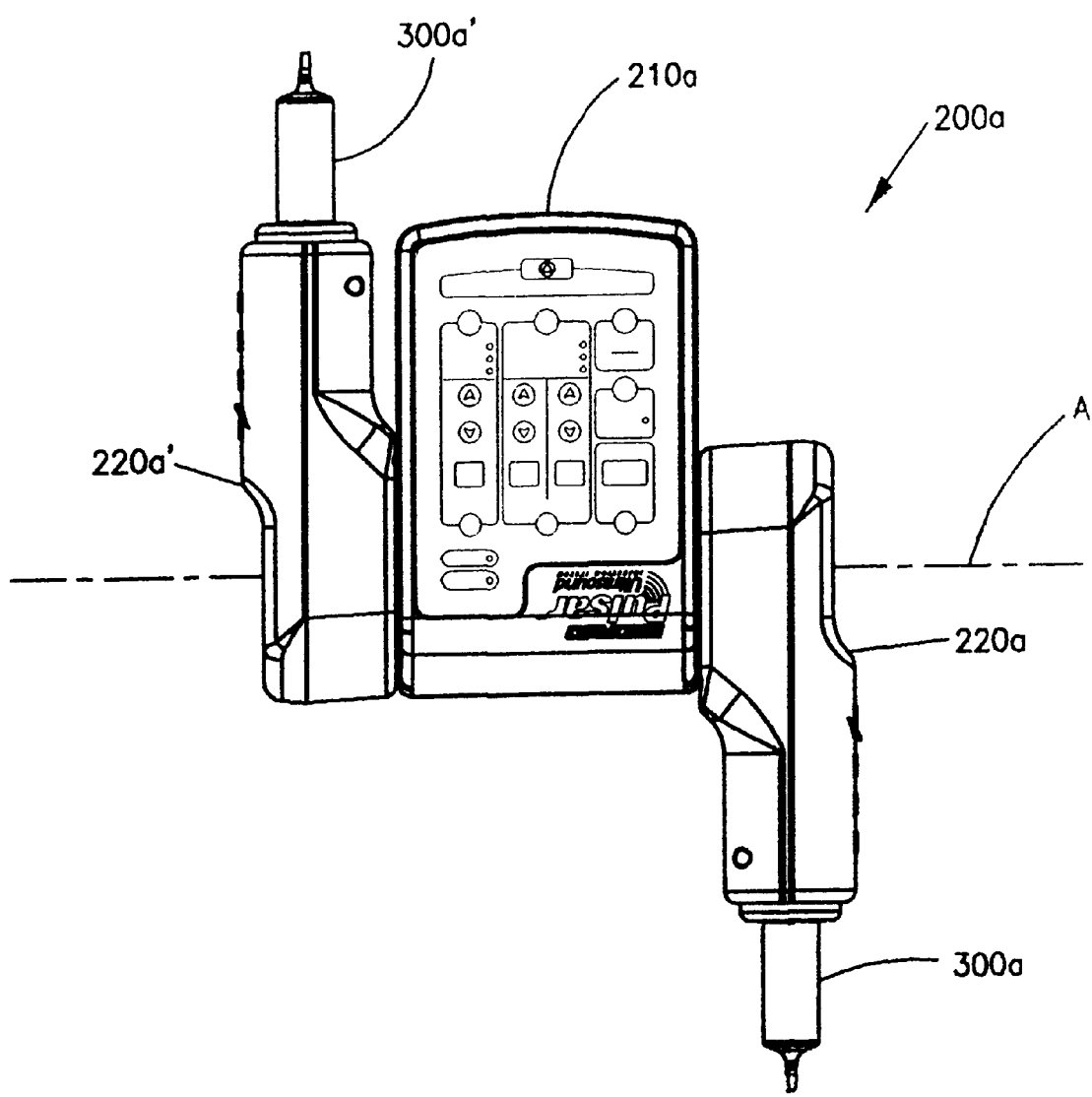
FIG. 7 illustrates an embodiment of an injector comprising two syringe interface modules rotatably connected to a control unit housing.
Figure 8:
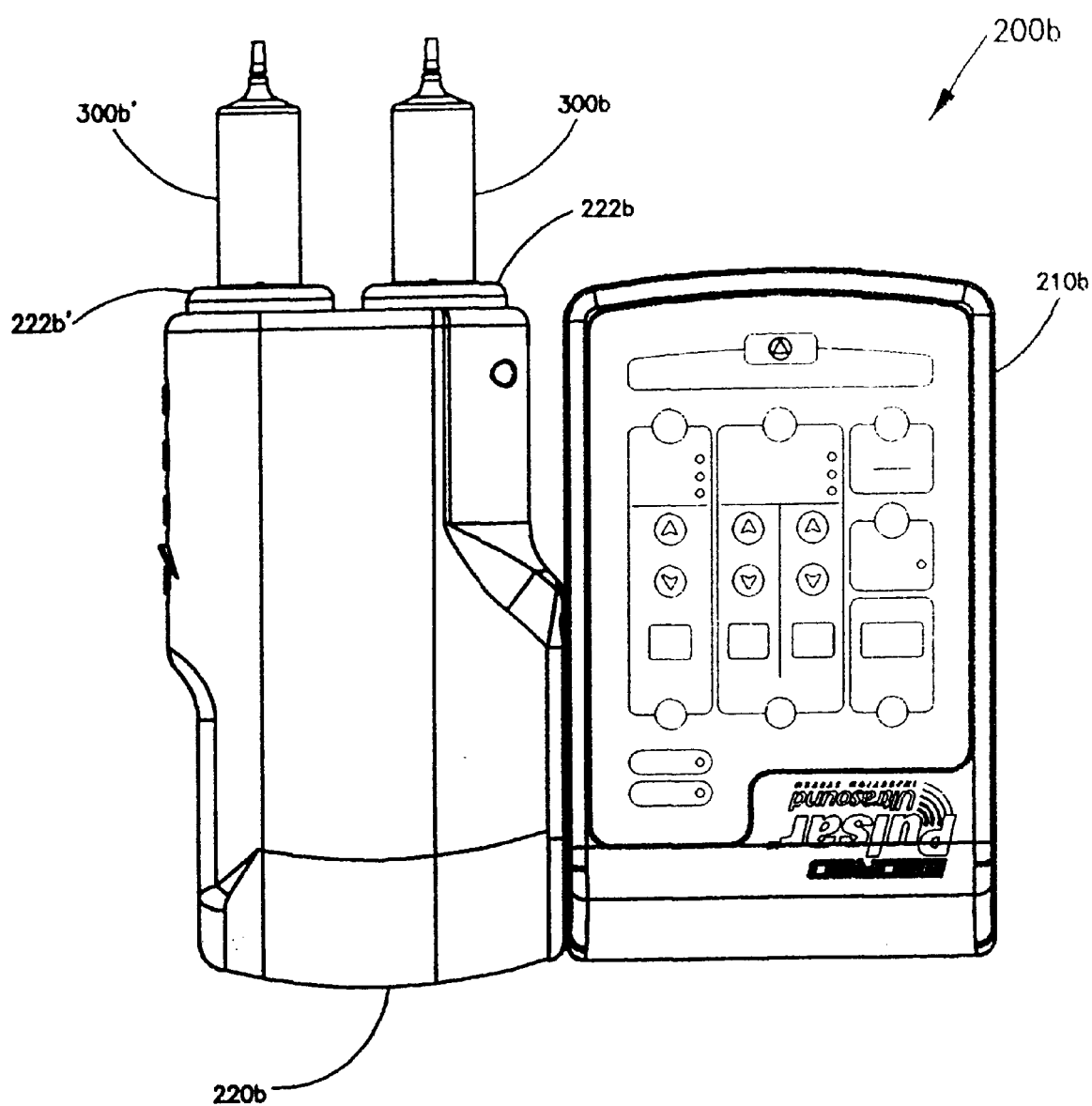
FIG. 8 illustrates an embodiment of an injector comprising a syringe interface module rotatably connected to a control unit housing and having two syringe interfaces.

FIG. 7 illustrates an embodiment of the present invention in which an injector system 200 a includes two syringe interface modules 220a and 220a' to which syringes 300a and 300a', respectively, are attached. Each of syringe interface modules 220a and 220a' are rotatably attached to control unit 210a about an axis A. In FIG. 7, syringe interface module 220a is rotated downward, while syringe interface module 220a' is rotate upward. FIG. 8 illustrates an embodiment in which an injector system 200b includes a syringe interface module 220b that includes two syringe interfaces 222b and 222b' to which syringes 300b and 300b', respectively, are connected. Syringe interface module 220b is rotatably connected to control unit 210b. Syringe interface module 220b preferably includes two drive members (not shown) housed therein for independent control of fluid injection from each of syringes 300b and 300b'.

Figure 9:
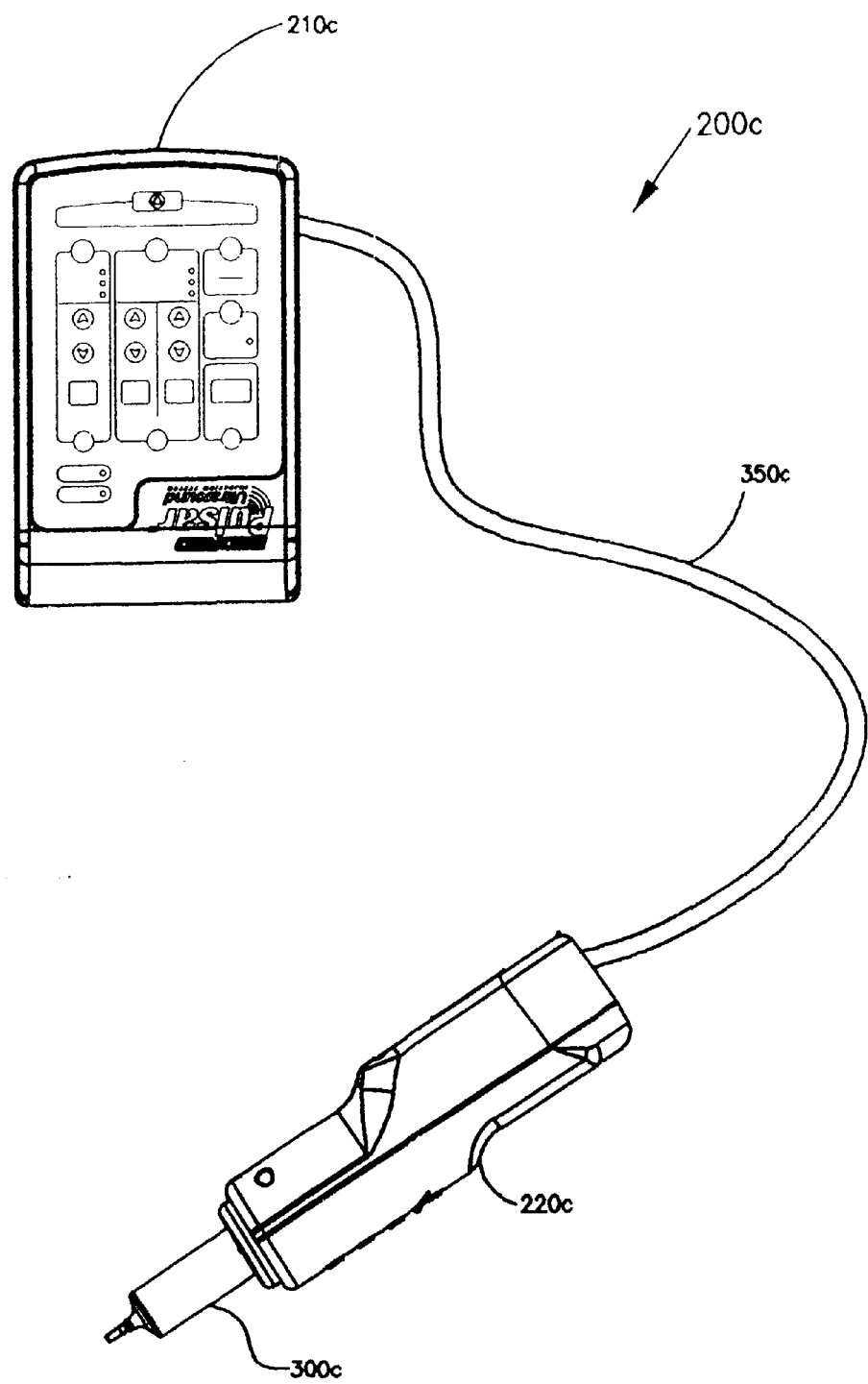
FIG. 9 illustrates an embodiment of an injector comprising a syringe interface module physically disconnected from a control unit housing.

FIG. 9 illustrates an embodiment of an injector system 200c including a syringe interface module 220c (with attached syringe 300c) that is physically disconnected from control unit 210c, but is in communicative connection with control unit 210c. In the embodiment of FIG. 9, syringe interface module 220c is in communicative connection with control unit 210c via communication line 350c, but the communication between control unit 210c and syringe interface module 220c can be wireless using wireless communication protocols as well known in the arts. In the embodiment of FIG. 9, syringe interface module 220c can be placed in virtually any position and/or orientation regardless of the position and/or orientation of control unit 210c. For example, the relatively small size and increased mobility (as compared to current injectors) of syringe interface module 220c enable syringe interface module 220c to be lain next to a patient.

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations which come within the meaning and range of equivalency of the claims are to be embraced within their scope.

What is claimed is:

1. An injector for use in injecting a fluid in a medical injection procedure, the injector comprising:
   a drive including a motor to pressurize the fluid;
   a sensor to provide a measure of fluid pressure; and
   a pressure monitor in communication with the sensor and the drive to stop the motor using 4-quadrant control when the sensor communicates a measured pressure of at least a pressure hazard limit, the pressure monitor also limiting power input to the motor to a power limit once the sensor communicates a measured pressure of at least a power limiting pressure, the power limiting pressure being below the pressure hazard limit.

2. The injector of claim 1 wherein the power limit is predetermined for the injector.

3. The injector of claim 1 wherein the power limit is set during operation of the injector when the power limit pressure is reached.

4. The injector of claim 1 wherein the pressure hazard limit is set during operation of the injector.

5. The injector of claim 1 wherein feedback from the sensor is used to perform a periodic recalibration.

6. The injector of claim 1 wherein the sensor measures force upon a component of the drive.

7. An injector system for use in injecting a fluid in a medical injection procedure, the injector comprising:

a motor to pressurize the fluid;

a servo controller in communication with the motor;

a sensor including a force transducer to provide a measure of fluid pressure; and a pressure monitor in communication with the sensor and the servo controller to stop the motor using 4-quadrant control when the sensor measures a pressure of at least a pressure hazard limit, the pressure monitor also limiting power input to the motor to a power limit when the sensor measures a pressure corresponding to a power limiting pressure, the power limiting pressure being below the pressure hazard limit.

8. The injector system of claim 7 wherein the servo controller limits power to the motor.

9. An injector system for use in injecting a fluid in a medical injection procedure, the injector system comprising:

a motor to pressurize the fluid;

a servo controller in communication with the motor;

a sensor in communication with the servo controller including a force transducer to provide a measure of fluid pressure; and a safety monitoring system in communication with the sensor, the safety monitoring system further being in communication with the servo controller, the safety monitoring system setting a pressure hazard limit and communicating the pressure hazard limit to the servo controller, the servo controller stopping the motor using 4-quadrant control when the sensor communicates a fluid pressure measurement of at least the pressure hazard limit.

10. The injector system of claim 9 wherein the safety monitoring system also sets a power limiting pressure that is less than the pressure hazard limit and communicates the power limiting pressure to the servo controller, the servo controller limiting the power to the motor when the sensor communicates a measured pressure of at least the power limiting pressure.

11. A method of controlling an injector system for use in a medical injection procedure, the method comprising the steps of:

measuring a variable that is proportional to fluid pressure;

limiting power input to a motor of the injector to a power limit once the variable reaches a value corresponding to at least a power limiting pressure; and stopping the motor using 4-quadrant control if the variable reaches a value corresponding to at least a pressure hazard limit, the pressure hazard limit being greater than the power limiting pressure.

12. The method of claim 11 wherein the variable is force exerted on a component of the injector system, the force being proportional to the fluid pressure.

13. The method of claim 11 wherein the step of stopping the motor includes the steps of setting a command position to a measured position when a stop command is issued, setting a command velocity to zero and subsequently setting the command position to a measured position when the motor stops.

* * * * *